(12) United States Patent
Thoene et al.

(10) Patent No.: US 9,023,798 B2
(45) Date of Patent: May 5, 2015

(54) CYSTINOSIN REPLACEMENT FACTOR

(75) Inventors: Jess Thoene, Ann Arbor, MI (US); Jeffrey Innis, Whitmore Lake, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 550 days.

(21) Appl. No.: 12/842,853

(22) Filed: Jul. 23, 2010

(65) Prior Publication Data

US 2011/0020411 A1 Jan. 27, 2011

Related U.S. Application Data

(60) Provisional application No. 61/228,327, filed on Jul. 24, 2009.

(51) Int. Cl.
| | | |
|---|---|---|
| *A61K 38/00* | (2006.01) | |
| *A61K 38/16* | (2006.01) | |
| *C07K 1/00* | (2006.01) | |
| *C12N 5/00* | (2006.01) | |
| *C12N 5/07* | (2010.01) | |
| *A61K 38/17* | (2006.01) | |
| *A61K 9/50* | (2006.01) | |

(52) U.S. Cl.
CPC ........... *A61K 38/1709* (2013.01); *A61K 9/5068* (2013.01)

(58) Field of Classification Search
CPC ....... A61K 38/00; A61K 35/12; C07K 14/47; C07K 14/705; C07K 14/4705; G01N 2800/042; G01N 33/5041
See application file for complete search history.

(56) References Cited

U.S. PATENT DOCUMENTS

| | | | | |
|---|---|---|---|---|
| 5,521,086 A | * | 5/1996 | Scott et al. | 435/254.2 |
| 5,618,682 A | | 4/1997 | Scheirer et al. | |
| 5,674,713 A | | 10/1997 | McElroy et al. | |
| 5,976,796 A | | 11/1999 | Szalay et al. | |
| 6,074,859 A | | 6/2000 | Hirokawa et al. | |
| 7,091,310 B2 | * | 8/2006 | Merzouk et al. | 530/300 |
| 7,652,070 B2 | * | 1/2010 | Rubin | 514/665 |
| 8,026,284 B2 | * | 9/2011 | Dohil et al. | 514/665 |
| 2006/0147431 A1 | | 7/2006 | Uchida et al. | |

FOREIGN PATENT DOCUMENTS

| | | |
|---|---|---|
| WO | 2006007560 A2 | 1/2006 |
| WO | 2007091250 A2 | 8/2007 |

OTHER PUBLICATIONS

Gahl 2003. Eur J. Pediatr. 162:S38-S41.*
Kalatzis et al. 2001. EMBO J. 20:5940-5949.*
Cherqui et al. 2001. J Biol Chem. 276:13314-13321.*
Haq et al. 2002. J Am. Soc. Nephrol. 13:2046-2051.*
Gao et al. 2005. FEBS J. 272:2497-2511.*
Cherqui et al. 2002. Mol. and Cell Biol. 22:7622-7632.*
Anderson et al., "Design, Synthesis, and Initial In Vitro Evaluation of Novel Prodrugs for the Treatment of Cystinosis," Lett Drug Design Discov, 3, pp. 336-345 (2006).
Ausubel et al., "Current Protocols in Molecular Biology," John Wiley and Sons, Ltd. (1995), Unit 2.1.
Gahl et al. "Cystinosis," New Engl J Med, 347, pp. 111-121 (2002).
Grady et al., "Patient in Experimental Gene Therapy Patient Dies, F.D.A. Says," New York Times, pp. 20 (Jul. 26, 2007).
Lemons et al., "Protein microinjection by protease permeabilization of fibroblasts," Anal Biochem, 172, pp. 219-227 (1988).
Lowry et al., "Protein measurement with the Folin phenol reagent," J Biol Chem, 193, pp. 265-275 (1951).
Martin, Remington's Pharmaceutical Sciences, 15th ed, Mack Publishing, (1975), Chapter 83.
Muenzer, et al. A phase I/II clinical trial of enzyme replacement therapy in mucopolysacchardidosis II (Hunter Syndrome), Mol Gen and Metab, 90, pp. 329-337 (2007).
Palacin et al., "Cystinuria," Metab Molec Basis of Inherited Disease, 8th ed, pp. 4909-4931, (2001).
Pisoni et al., "A Cystine-Specific Lysosomal Transport System Provides a Major Route for the Delivery of Thiol to Human Fibroblast Lysosomes: Possible Role in Supporting Lysosomal Proteolysis," J Cell Biol, 110, pp. 327-335 (1990).
Sambrook et al., "Molecular Cloning: A Laboratory Manual (3rd Edition)" (2001), A8.50.
Shotelersuk et al., "CTNS mutations in American-based population of cystinosis patients," Am J Hum Genet, 63, pp. 1352-1362, (1998).
Thoene, "A Review of the Role of Enhanced Apoptosis in the Pathophysiology for the Treatment of Cystinosis," Mol Genet Matab., 92, pp. 292-298 (2007).
De Wet et al., "Firefly Luciferase Gene: Structure and Expression in Mammalian Cells," Mol Cell Biol, 7, pp. 725-737 (1987).
Taranta A. et al. "Identification and subcellular localization of a new cystinosin isoform" Am J Physiol Renal Physiol., May 2008, 294(5): 1101-1108.
Ohtaki et al., "Expression, Purfication, and Reconstitution of Receptor for Adenylate Cyclase-activating Polypeptide." J Biol Chem. 1998, 273(25):15464-15473.

\* cited by examiner

*Primary Examiner* — Shulamith H Shafer

(74) *Attorney, Agent, or Firm* — Casimir Jones S.C.

(57) ABSTRACT

The present invention provides compositions and methods for providing factor replacement therapy. In particular, the present invention provides replacement therapy for subjects suffering from cystinosis.

10 Claims, 13 Drawing Sheets

FIGURE 3
A)
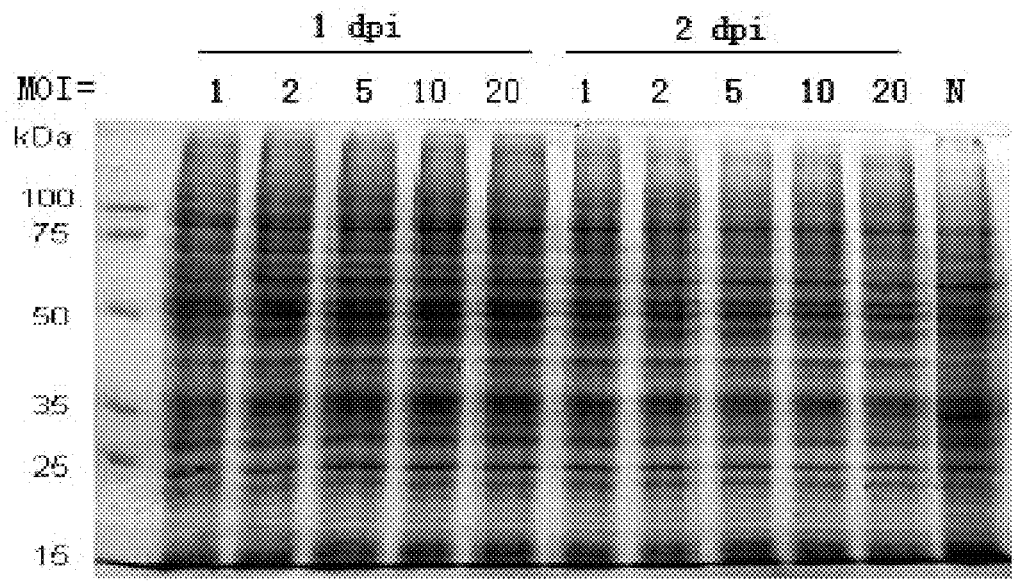
B)
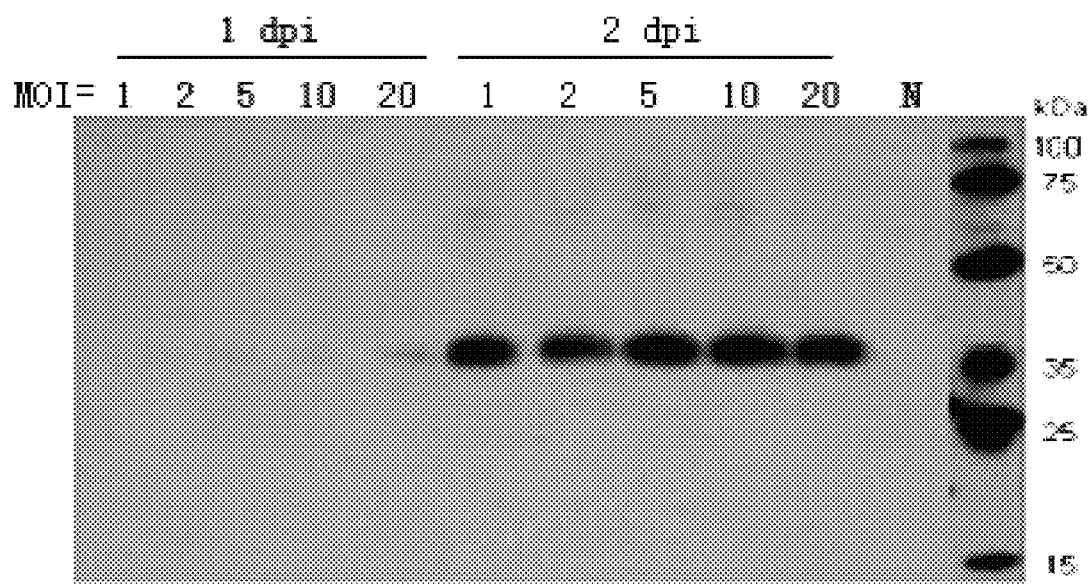

FIGURE 3 (cont'd)
C)
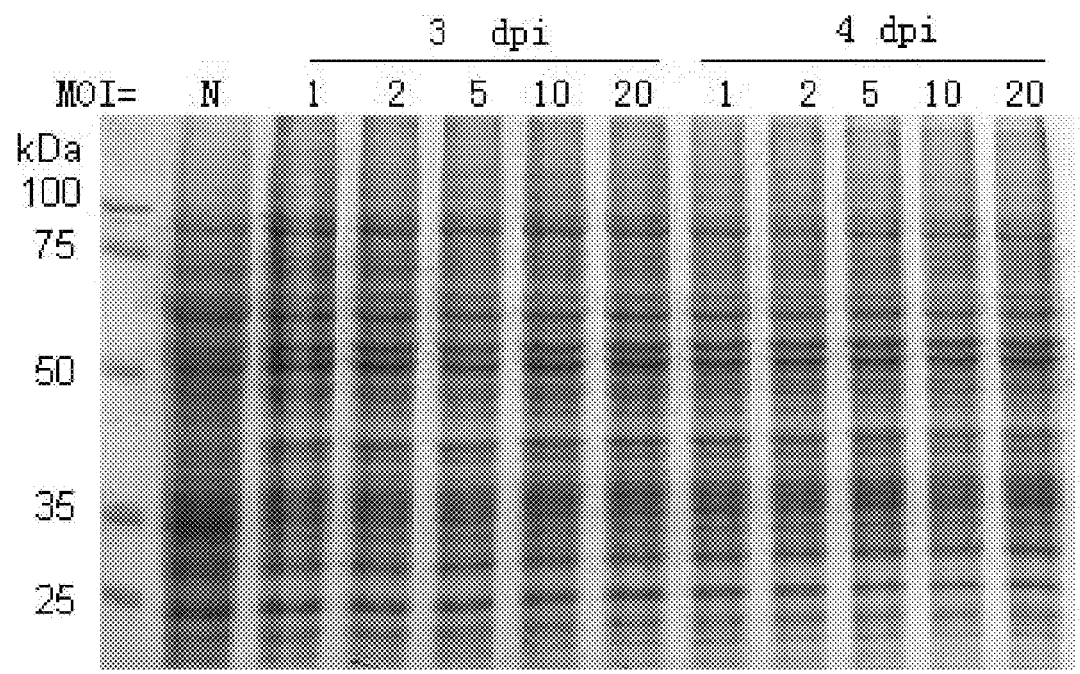
D)
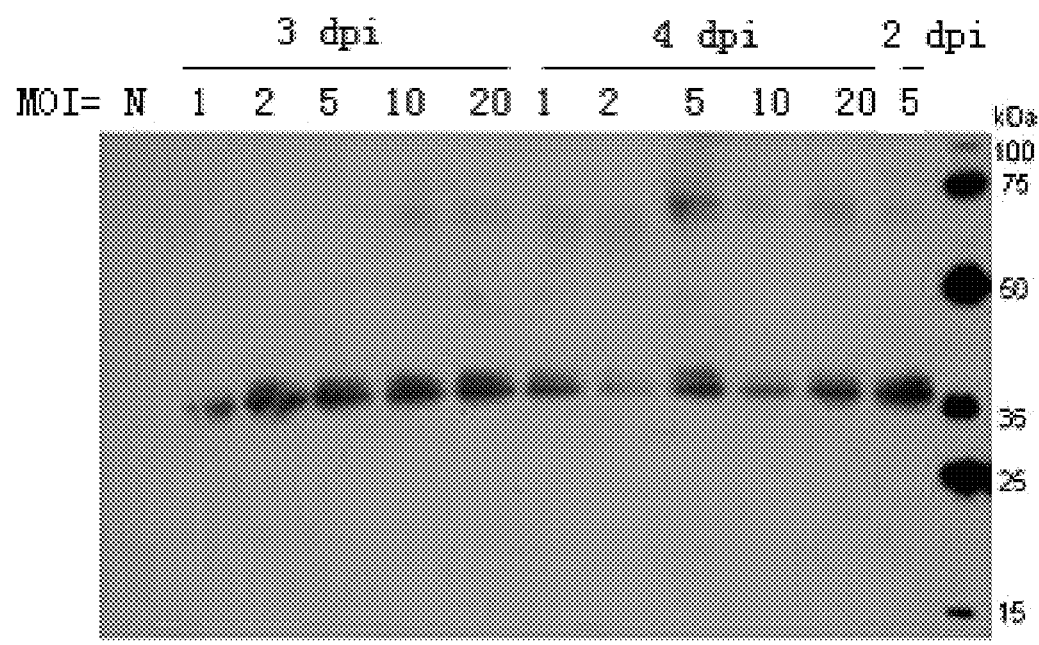

FIGURE 4
A)
B)
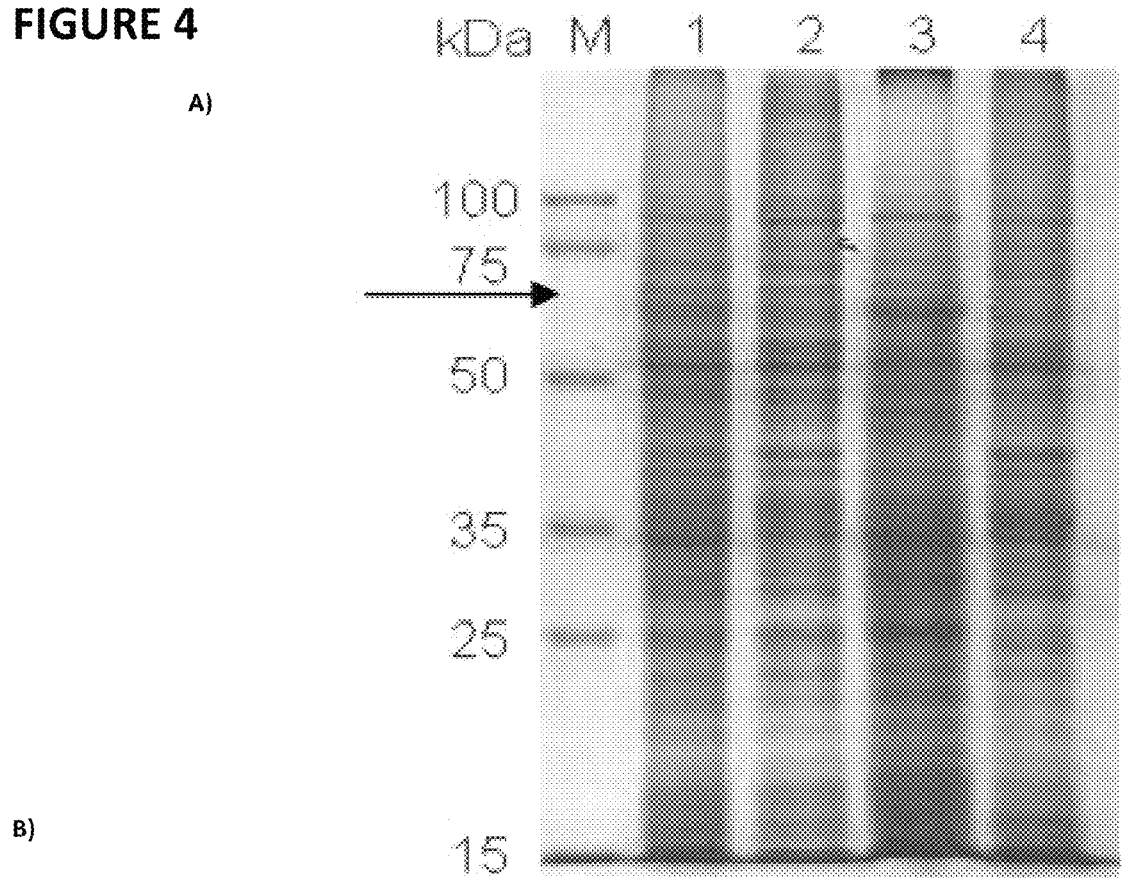
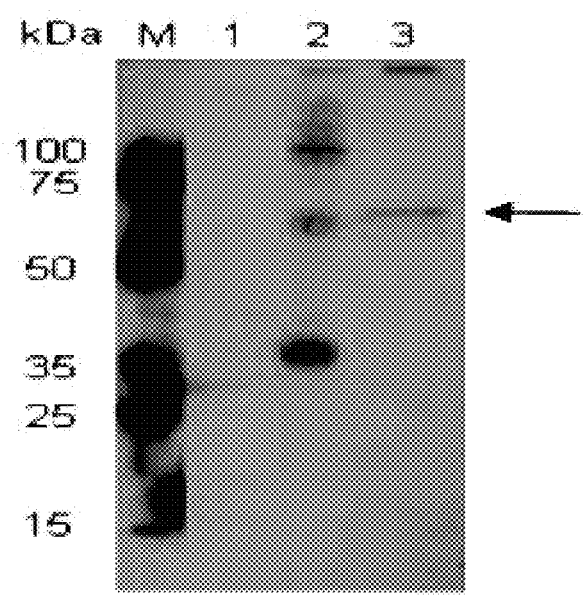

FIGURE 5
A)
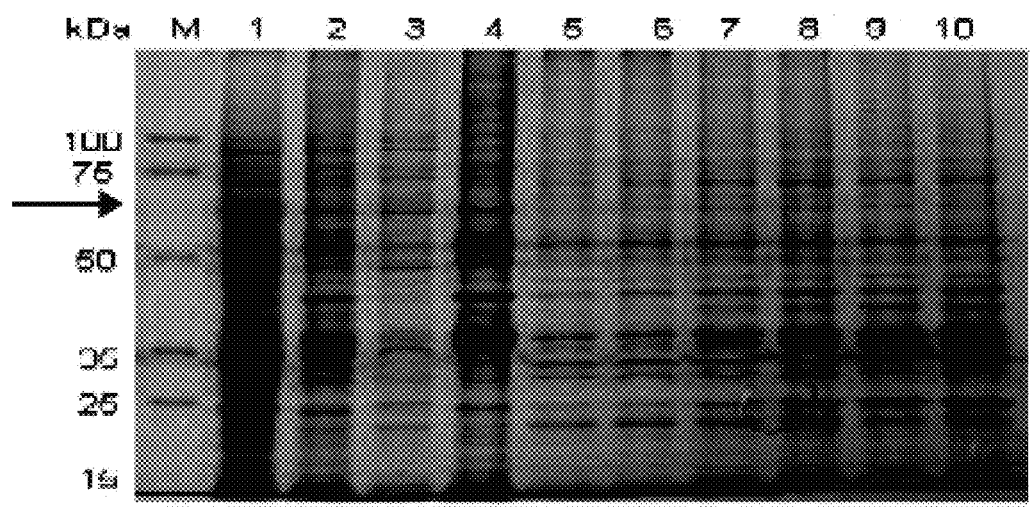
B)
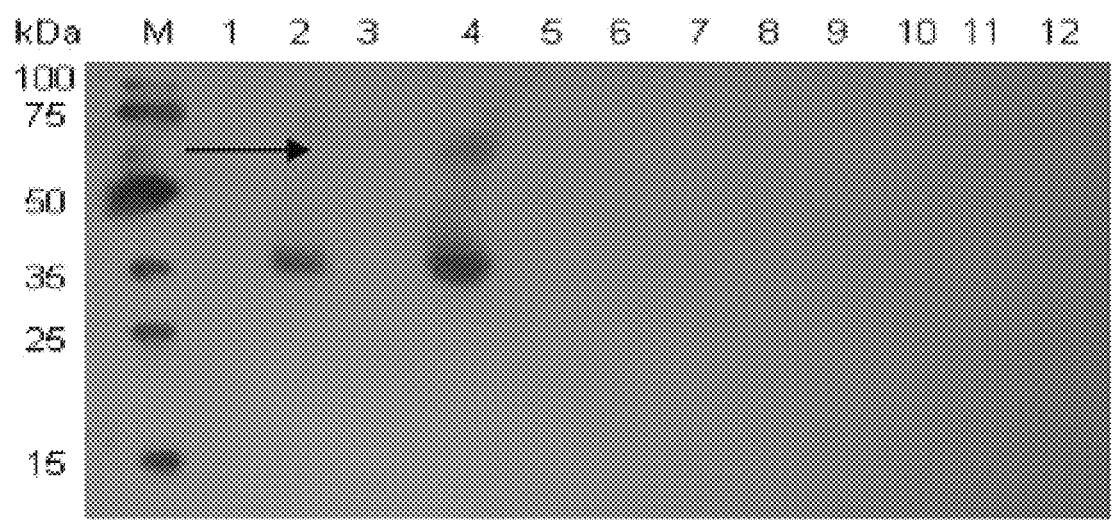

FIGURE 7
A)
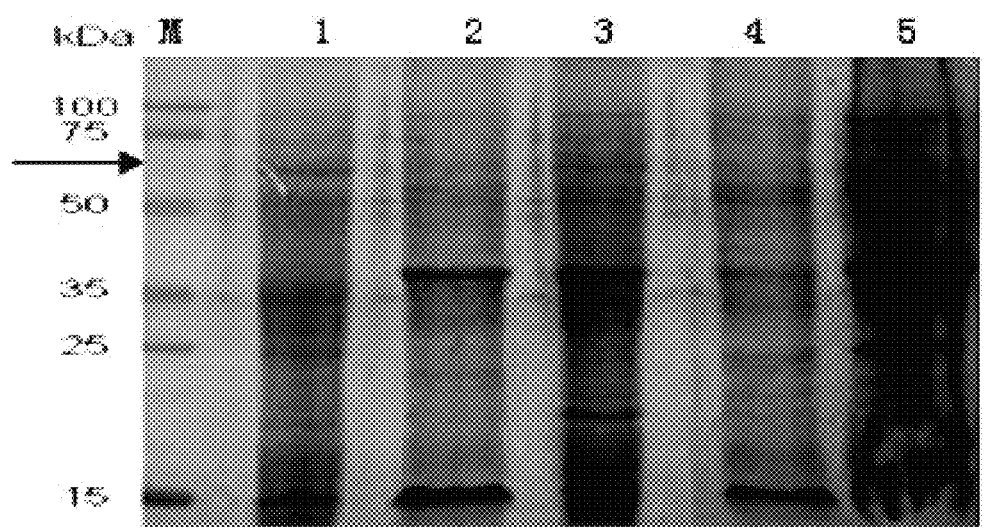
B)
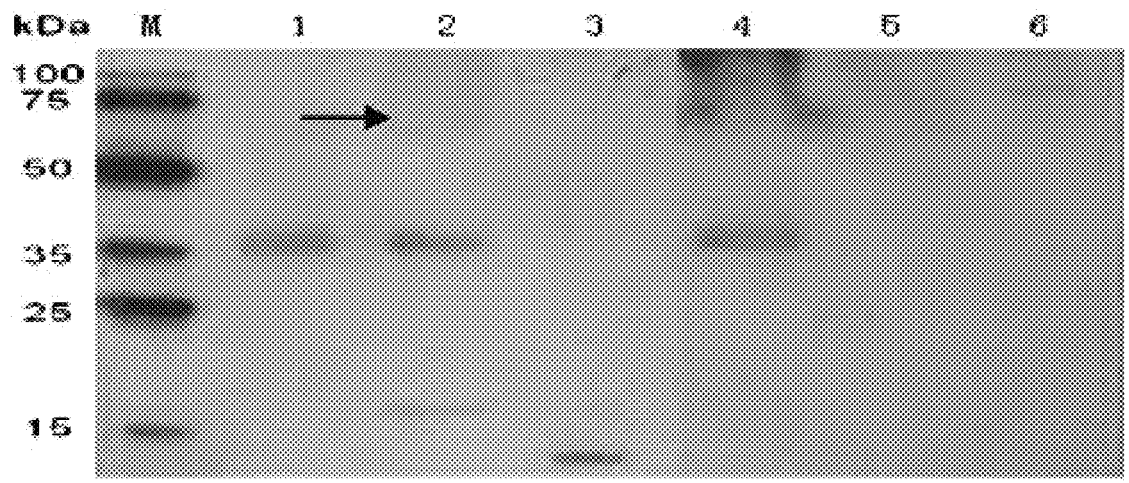

FIGURE 8
A)
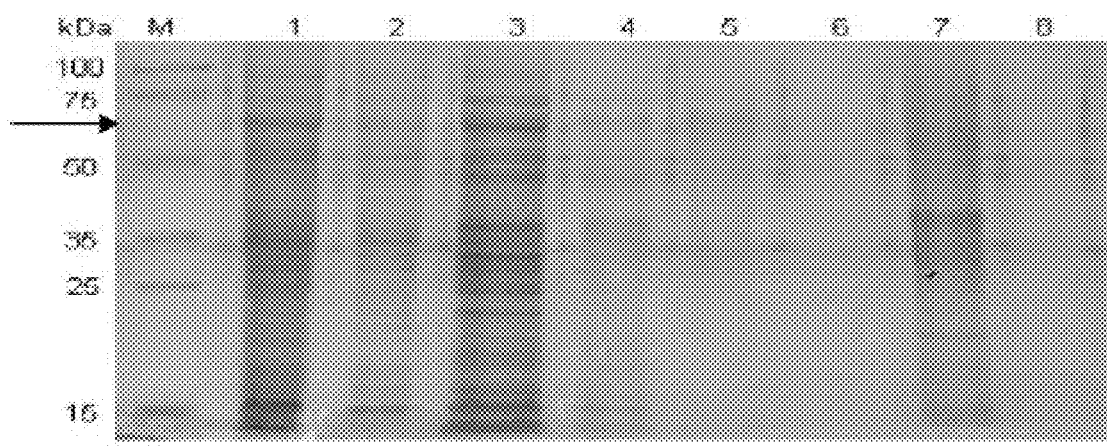
B)
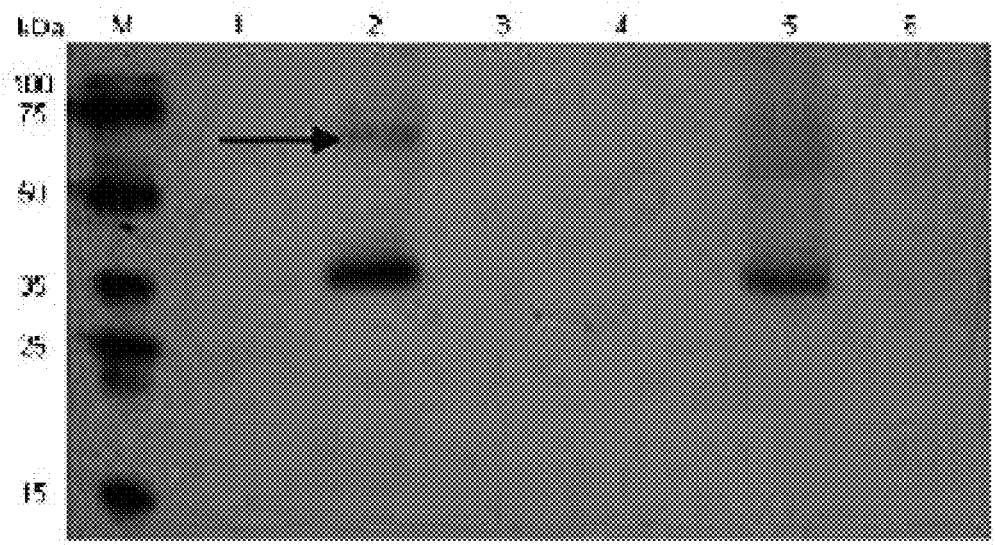

FIGURE 9
A)
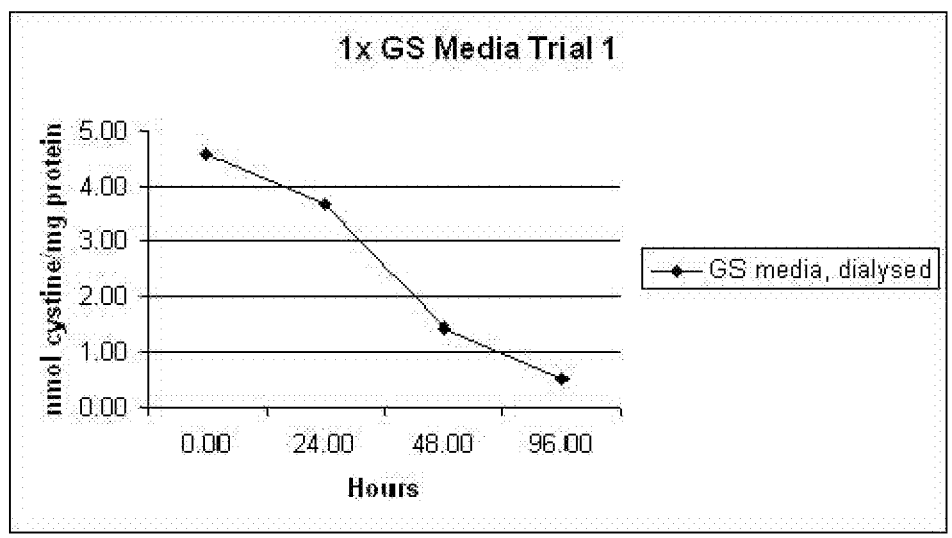
B)
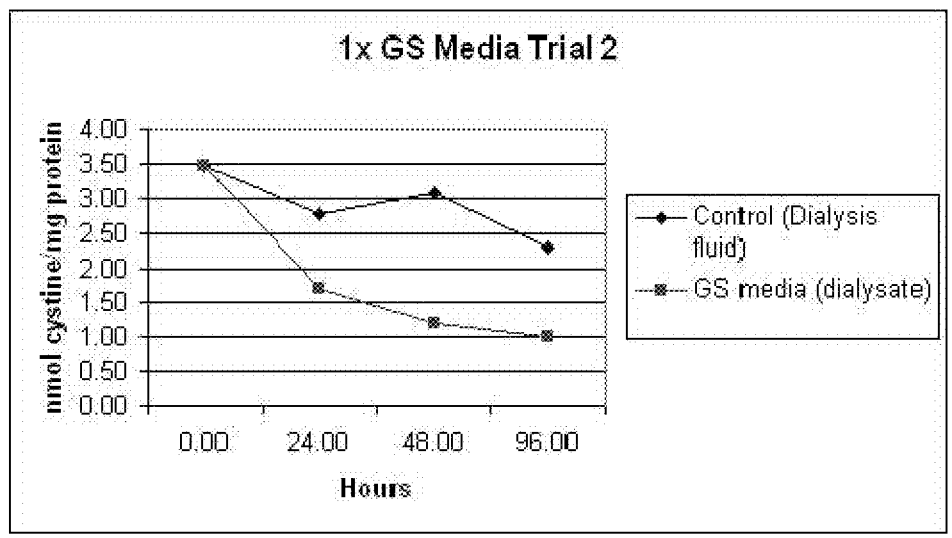

Figure 11

Cystine Depletion

Bar chart (rotated) showing cystine depletion at 96 hours, with x-axis "nmol cystine/ mg protein, fraction of t-0" ranging from 0.00 to 0.80. Bars from top to bottom:
- saliin medium, supernatant
- saliin medium, sedimentable fraction
- cystinosin medium, supernatant
- cystinosin medium, sedimentable fraction
- saliin medium, dialysis fluid
- saliin medium, dialysate
- cystinosin medium, dialysis fluid
- cystinosin medium, dialysate

Figure 12

Sialic Acid Depletion at 96 hours

Bars (top to bottom as displayed):
- sialin medium, supernatant
- sialin medium, sedimentable fraction
- cystinosin medium, supernatant
- cystinosin medium, sedimentable fraction
- sialin medium, dialysis fluid
- sialin medium, dialysate
- cystinosin medium, dialysis fluid
- cystinosin medium, dialysate x-axis: nmol SA/mg protein, fraction of t-O (0.00 to 1.60)

ns on the intact lysine transporter. Unfortunately, the structure of cysteamine includes a free thiol group, thus the drug has the odor and taste of rotten eggs, a feature of concern both to parents administering the treatment to children, and to patients themselves who may find the offensive odor to be socially debilitating. Although cysteamine has been FDA approved since 1994, there are problems with this therapy: 1) It does not prevent renal failure, but merely delays the onset, for most patients 2) its repugnant thiol odor and taste causes both gastrointestinal and compliance problems and social concerns in children as they reach adolescence. The latter issue causes some patients to forgo or discontinue treatment, with the expected concomitant health consequences resulting therefrom. For these reasons, a superior form of treatment that averts renal failure indefinitely, and which lacks the thiol odor and taste of cysteamine would be highly desirable.

CYSTINOSIN REPLACEMENT FACTOR

CROSS-REFERENCE TO RELATED APPLICATION

The present application claims priority to U.S. Provisional Application 61/228,327, filed Jul. 24, 2009, which is herein incorporated by reference in its entirety.

FIELD OF THE INVENTION

The present invention provides compositions and methods for providing factor replacement therapy. In particular, the present invention provides replacement therapy for subjects suffering from cystinosis.

BACKGROUND OF THE INVENTION

Cystinosis has been known since the first decade of the last century. Small, pale children who died of wasting and whose organs were shown to be riddled with microscopic crystals were described by Abderhalden in 1903. He termed the condition "Familiare Cystindiathese" (Thoene. Mol Genet Metab. 2007, herein incorporated by reference in its entirety). The disease has been conflated with the unrelated condition cystinuria, which is an extracellular disease of renal transport which results in excess cystine urinary excretion, leading to cystine stones in the urinary tract (Palacin et al., eds. The Metabolic and Molecular Bases of Inherited Disease, 8$^{th}$ edition, McGraw Hill, 4909-4932, 2001, herein incorporated by reference in its entirety), while cystinosis is an intracellular condition that results from defective lysosomal cystine transport, leading to lysosomal cystine storage. The lysosomal cystine transporter, cystinosin, is encoded by CTNS, located at 17 p 13.3, and functions to move cystine from the lysosomal interior to the cytosol, where it can be reused for GSH and protein synthesis. Many mutations have been described at this locus, however a large 57 kb deletion accounts for about half the cases descended from west European parents. The clinical phenotype in nephropathic cystinosis is relatively unique: renal Fanconi syndrome with salt, water, glucose, amino acid and other small molecule losses; crystalline keratopathy and salt and pepper retinopathy; short stature and failure to thrive; photophobia; and ultimately renal death by age 10 years. Other elements include hypothyroidism, and later in life, muscle weakness, esophageal dysmotility, and diabetes. It produces the renal Fanconi syndrome with salt, water and other small molecule wasting, deficient bone mineralization, short stature, failure to thrive, and later in life, hypothyroidism, muscle wasting and weakness, esophageal dysmotility, pancreatic deficiency, and pulmonary involvement. It is treated symptomatically with salt and water replacement, and specifically, with cysteamine, which causes depletion of the stored lysosomal cystine which is the biochemical hallmark of the condition and which results from mutations in the lysosomal cystine transporter, cystinosin. Therapy of cystinosis has taken several forms, although none is currently satisfactory. Initially recognition of the peril these children are in from the risk of dehydration and electrolyte imbalance led to symptomatic water and electrolyte replacement therapy. Subsequently, chronic dialysis and then renal transplantation were used to compensate for the renal failure. Specific therapy for cystinosis was achieved in 1994 when the FDA approved cysteamine bitartrate as Cystagon for the treatment of cystinosis. This drug causes depletion of cystine from cystinotic lysosomes by forming a mixed disulfide with cystine which resembles lysine and which can thus exit lyso- Gene therapy has been proposed to treat a variety of conditions, including inborn errors of metabolism, however serious reactions to AV and AAV vectors has lead to questioning in the field as whether these agents can be safely employed in patients. Gene therapy, long the hope of patients with many diseases, both genetic and otherwise, has continuing issues of safety and efficacy. The safety concerns relate to integration of the trans genes in locations that disrupt the function of critical tumor supressors, or other vital sequences. Other side effects include serious or fatal allergic reactions to the large number of virions which must be administered in the quest for stable gene expression that will have a salutary impact on phenotype. A death was reported in July, 2007 in an arthritis patient receiving gene therapy using an AAV vector, which was hoped to be safer than the AV vector involved in the Geissinger death in 1999.

SUMMARY

In some embodiments, the present invention provides compositions and methods for treating factor deficiency (e.g. cystinosin deficiency) in a subject. In some embodiments, the present invention provides compositions and methods for depleting cystine from lysosomes (e.g. cystinotic lysosomes). In some embodiments, the present invention provides compositions comprising a cystine depletion factor (CDF) and methods of preparation (e.g. transfection, expression, purification, etc.) and use (e.g. therapeutic administration, prophylactic administration, etc.) thereof. In some embodiments, the present invention provides compositions comprising a cystinosin replacement factor and methods of preparation (e.g. transfection, expression, purification, etc.) and use (e.g. therapeutic administration, prophylactic administration, etc.) thereof. In some embodiments, the present invention provides compositions comprising cystinosin and methods of preparation (e.g. transfection, expression, purification, etc.) and use (e.g. therapeutic administration) thereof. In some embodiments, the present invention provides compositions and methods for treating cystinosis in a subject (e.g. administration of CDF). In some embodiments, the present invention provides exosomes (e.g. comprising cystinosin) for use in treating a disease or disorder (e.g. cystinosis).

In some embodiments, the present invention provides compositions comprising a cystine depletion factor (CDF). In some embodiments, the CDF reduces the level of cystine in lysosomes. In some embodiments, the CDF reduces the level of cystine in cystinotic lysosomes. In some embodiments, the CDF reduces the level of cystine in lysosomes to a normal, healthy, and/or non-cystinoic level. In some embodiments, the CDF is secreted from cells expressing cystinosin. In some embodiments, the CDF functions as a replacement for cystinosin in a subject suffering from cystinosis. In some embodiments, administration of the CDF to a subject suffering from cystinosis provides treatment (e.g. curative and/or palliative) for cystinosis. In some embodiments, the CDF depletes cystine from lysosomes (e.g. cystinotic lysosomes) through the same mechanism as cystinosin (e.g. endogenous cystinosin in a subject not suffering from cystinosin). In some embodiments, the CDF depletes cystine from lysosomes (e.g. cystinotic lysosomes) through a different mechanism than cystinosin. In some embodiments, the CDF comprises one or more small molecules, proteins, peptides, macromolecules, complexes, etc. In some embodiments, CDF comprises, consists essentially of, or consists of cystinosin.

In some embodiments, the present invention provides a cystinosin replacement factor (CRF). In some embodiments, the CRF functions as a replacement for cystinosin in a subject suffering from cystinosis. In some embodiments, administration of the CRF to a subject suffering from cystinosis provides treatment (e.g. curative and/or palliative) for cystinosis. In some embodiments, the CRF depletes cystine from lysosomes (e.g. cystinotic lysosomes) through the same mechanism as cystinosin (e.g. endogenous cystinosin in a subject not suffering from cystinosis). In some embodiments, the CRF is secreted from cells expressing cystinosin. In some embodiments, the CRF reduces the level of cystine in lysosomes. In some embodiments, the CRF reduces the level of cystine in cystinotic lysosomes. In some embodiments, the CRF comprises one or more small molecules, proteins, peptides, macromolecules, complexes, etc. In some embodiments, the CRF comprises, consists essentially of, or consists of cystinosin.

In some embodiments, the present invention provides a composition comprising cystinosin. In some embodiments, the cystinosin is purified or partially purified. In some embodiments, the cystinosin is isolated or partially isolated. In some embodiments, the cystinosin is recombinantly expressed. In some embodiments, the cystinosin is produced in cells transfected with the CTNS gene or variants thereof. In some embodiments, the present invention provides a composition comprising purified and soluble recombinant cystinosin. In some embodiments, the recombinant cystinosin functions as a replacement for endogenous cystinosin in a subject suffering from cystinosis. In some embodiments, cystinosin is complexed with one or more additional, agents, compounds, peptides, macromolecules, complexes, etc.

In some embodiments, the present invention provides cystinosin-expressing cells. In some embodiments, cells express recombinant cystinosin. In some embodiments, cells are transfected with the gene for cystinosin (CTNS) or variants thereof. In some embodiments, cells secrete cystinosin, CRF, and/or CDF. In some embodiments, cells secrete or otherwise generate exosomes comprising cystinosin, CRF, and/or CDF.

In some embodiments, the present invention provides compositions and methods for treating cystinosis. In some embodiments, the present invention provides a method for treating cystinosis comprising administering an isolated portion of liquid media, within which cells expressing cystinosin were grown, to subjects suffering from cystinosis. In some embodiments, the isolated portion of the liquid media provides a replacement for cystinosin. In some embodiments, the isolated portion of the liquid media undergoes a purification step prior to administering to the subject.

In some embodiments, the present invention provides a method for treating cystinosis comprising administering recombinant cystinosin to a subject suffering from cystinosis. In some embodiments, the recombinant cystinosin is expressed in cells. In some embodiments, the cells comprise Sf9 insect cells. In some embodiments, the cells are grown in liquid media. In some embodiments, the recombinant cystinosin is obtained from the liquid media. In some embodiments, the recombinant cystinosin is purified from the liquid media. In some embodiments, the recombinant cystinosin functions as a replacement for endogenous cystinosin in a subject suffering from cystinosis.

In some embodiments, the present invention provides a factor replacement therapy comprising: a) expressing the factor in cells, wherein the cells are grown in liquid media, and b) administering an isolated portion of the liquid media to a subject lacking the factor. In some embodiments, the isolated portion of said liquid media comprises elements purified from the liquid media. In some embodiments, the factor provides a supplement to the subject lacking the factor. In some embodiments, the isolated portion of said liquid media comprises compositions which compensate for the factor in the subject lacking the factor. In some embodiments, the factor comprises cystinosin. In some embodiments, the subject suffers from cystinosis. In some embodiments, administering of the isolated portion of the liquid media provides a replacement for cystinosin in the subject. In some embodiments, the isolated portion of the liquid media comprises recombinant cystinosin.

In some embodiments, the present invention provides a composition comprising cystinosin replacement factor, wherein the cystinosin replacement factor functions as a replacement for endogenous cystinosin in a subject suffering from cystinosis. In some embodiments, the cystinosin replacement factor is configured to deplete cystine from cystinotic lysosomes. In some embodiments, the cystinosin replacement factor is obtained from a liquid media in contact with cells expressing recombinant cystinosin. In some embodiments, the cystinosin replacement factor comprises recombinant cystinosin. In some embodiments, all or a portion of the recombinant cystinosin is encapsulated within one or more exosomes. In some embodiments, the composition further comprises a pharmaceutically acceptable buffer.

In some embodiments, the present invention provides a method for treating cystinosis, comprising: administering an isolated portion of liquid media, within which cells expressing cystinosin were grown, to subjects suffering from cystinosis. In some embodiments, the isolated portion of liquid media comprises a cystine depletion factor. In some embodiments, the isolated portion of liquid media comprises a sedimentable fraction of the liquid media. In some embodiments, the cystine depletion factor comprises exosomes. In some embodiments, the exosomes comprise cystinosin. In some embodiments, the isolated portion of the liquid media undergoes one or more purification steps prior to administering to said subject. In some embodiments, the isolated portion of the liquid media is combined with a pharmaceutically acceptable buffer. In some embodiments, the isolated portion of the liquid media provides a replacement for endogenous cystinosin.

In some embodiments, the present invention provides a method for treating cystinosis comprising administering recombinant cystinosin to a subject suffering from cystinosis. In some embodiments, the recombinant cystinosin is expressed in cells. In some embodiments, the cells comprise Sf9 cells. In some embodiments, the cells are grown in liquid media. In some embodiments, the recombinant cystinosin is purified from said liquid media. In some embodiments, the recombinant cystinosin sedimented by centrifugation. In some embodiments, the recombinant cystinosin is encapsulated in exosomes. In some embodiments, the recombinant cystinosin functions as a replacement for endogenous cystinosin in a subject suffering from cystinosis.

In some embodiments, the present invention provides compositions and methods for factor replacement therapy. In some embodiments, a factor is produced and administered to a subject deficient in the factor as a treatment for the deficiency. In some embodiments, the factor is expressed in cells. In some embodiments, the factor is a protein or peptide. In some embodiments, the factor is secreted from cells in exosomes. In some embodiments, the factor is encapsulated in exosomes. In some embodiments, the present invention provides exosomes comprising a replacement factor. In some embodiments, the present invention provides administering exosomes comprising a replacement factor to a subject deficient in that subject as a treatment for factor deficiency and/or related conditions and/or symptoms.

BRIEF DESCRIPTION OF THE DRAWINGS

The foregoing summary and detailed description is better understood when read in conjunction with the accompanying drawings which are included by way of example and not by way of limitation.

FIG. 3 shows MOI optimization: 10 ml $2*10^6$/ml sf9 cells were infected at the MOI of 1, 2, 5, 10 and 20 separately, and each 1 ml cell pellet was collected 1 dpi, 2 dpi, 3 dpi and 4 dpi. The cells were analyzed by SDS-PAGE and western blot.

FIG. 4 shows an (A) SDS-PAGE and (B) Western blot analysis of a protein solubility test: 200 ml infected sf9 cells were collected and washed by PBS once; the cells were suspended with 20 mM Tris.HCl, 1 mM DTT, 1% NP-40, pH8.0 on ice for 45 min and sonicated. The supernatant and the pellet were separated at the speed of 12,000 rpm for 10 min at 4° C. SDS-PAGE (A) and western blot analyzed the solubility of the protein. Lane 1: Sf9 bacmid, Lane 2: whole cell lysate, Lane 3: cytosol treated with 20 mM Tris-HCl 1 mM DTT 1% NP-40 pH8, and Lane 4: pellet.

FIG. 5 shows a (A) SDS-PAGE and (B) Western blot analysis of an extraction test in which cell pellet was treated with Buffer A (10 mM HEPES-KOH, pH7.9 at 4° C., 1.5 mM MgCl2, 10 mM KCl, 1 mM PMSF) on ice for 45 min, the supernatant and the pellet was separated, the buffer C (20 mM HEPES-KOH, pH7.9, 25% glycerol, 420 mM NaCl, 1.5 mM MgCl2, 1.5 mM MgCl2) then was followed. The obtained pellet from Buffer C was aliquot into 6 parts, and treated with the buffers (20 mM Tris.HCl, 2% TritonX-100 1% deoxycholate, 1 mM beta-mercaptoethanol, 5% Glycerol) of different pH and different concentration of NaCl. (A) Lane 1: whole cell lysate of Bacmid, Lane 2: pellet treated with 20 mM Tris-HCl 1 mM DTT 1% NP-40 pH 8, Lane 3: cytosol treated with Buffer A, Lane 4: cytosol treated with Buffer C, Lane 5: cytosol treated with 150 mM NaCl pH 7.5, Lane 6: cytosol treated with 150 M NaCl pH 10, Lane 7: cytosol treated with 500 mM NaCl pH 7.5, Lane 8: cytosol treated with 500 mM NaCl pH 10, Lane 9: cytosol treated with 1M NaCl pH 7.5, Lane 10: cytosol treated with 1M NaCl pH 10. (B) Lane 1: whole cell lysate of Bacmid, Lane 2: whole cell lysate of 44783, Lane 3: cytosol treated with 20 mM Tris-HCl 1 mM DTT 1% NP-40 pH 8, Lane 4: pellet treated with 20 mM Tris-HCl 1 mM DTT 1% NP-40 pH 8, Lane 5: cytosol treated with Buffer A, Lane 6: cytosol treated with Buffer C, Lane 7: cytosol treated with 150 mM NaCl, pH 7.5, Lane 8: cytosol treated with 150 mM NaCl, pH 10, Lane 9: cytosol treated with 500 mM NaCl, pH 7.5, Lane 10: cytosol treated with 500 mM NaCl, pH 10, Lane 11: cytosol treated with 1M NaCl, pH 7.5, Lane 12: cytosol treated with 1M NaCl pH 10. The SDS-PAGE (A) and Western blot (B) result shows the target protein was not dissolved in any buffer.

FIG. 7 shows (A) SDS-PAGE and (B) Western blot analysis of protein extraction with SKL and thiourea: infected cells were treated with 20 mM Tris-HCl 0.03% SKL pH8.0; the infected cell was then treated with 20 mM Tris-HCl 0.5% CHAPS 20 mM DTT, 0.4% ABS14, 2M thiourea, 6M urea pH8.0, the result shows that the protein in insoluble: Lane 1: whole cell lysate, Lane 2: pellet treated with 20 mM Tris-HCl 0.03% SKL pH 8, Lane 3: cytosol treated with 20 mM Tris-HCl 0.03% SKL pH 8, Lane 4: pellet treated with 20 mM Tris-HCl 0.5% CHAPS 20 mM DTT 0.4% ABS14 2M thiourea 6M urea pH 8, Lane 5: cytosol treated with 20 mM Tris-HCl 0.5% CHAPS 20 mM DTT 0.4% ABS142M thiourea 6M urea pH 8, and Lane 6 (B only): Sf9 bacmid.

FIG. 8 shows (A) SDS-PAGE and (B) Western blot analysis of Gu.HCl treatment and purification. Infected cells were extracted with 20 mM Tris-HCl 500 mM NaCl 2% TritonX-100 1% deoxycholate 1 mM BME 5% Glycerol pH 7.5 once, and then treated with 6M Gu.HCl. The supernatant was loaded on the Nickel column, eluted with 20 mM imidazole and 250 mM imidazole. The solutions obtained were diazlyzed against 20 mM Tris-HCl, 150 mM NaCl, 10% glycerol, but the precipitate produced. Protein was eluted with 20 mM imidazole, but was precipitated when renaturing. (A) Lane 1: whole cell lysate of Bacmid, Lane 2: whole cell lysate of 44783, Lane 3: cytosol treated with 20 mM Tris.HCl 500 mM NaCl 2% TritonX-100 1% deoxycholate, 1 mM BME 5% Glycerol pH 7.5, Lane 4: cytosol treated with PBS, Lane 5: pellet treated with 6M Gu.HCl, Lane 6. Eluted with 20 mM Tris.HCl 150 mM NaCl 6M Gu.HCl 10% Glycerol 20 mM Imidazole pH 8, Lane 7: pellet produced during the dialysis, Lane 8: Eluted with 20 mM Tris.HCl 150 mM NaCl 6M Gu.HCl 10% Glycerol 250 mM Imidazole pH 8. (B) Lane 1: Sf9bacmid, Lane 2: whole cell lysate, Lane 3: pellet treated with 6M Gu.HCl, Lane 4: Eluted with 20 mM Tris-HCL 150 mM NaCl 6M Gu.HCl 10% Glycerol 20 mM Imidazole pH 8, Lane 5: pellet produced during the dialysis, Lane 6: Eluted with 20 mM Tris-HCL 150 mM NaCl 6M Gu.HCl 10% Glycerol 250 mM Imidazole pH 8.

FIG. 9 shows cystine depletion of cystinotic fibroblasts by treatment with media from Sf9 cells expressing human cystinosin. 10 ml of medium removed from Sf9 cells transfected with CTNS-containing Bacmid was dialyzed against 500 ml Ham's F12 medium for 24 hours using regenerated cellulose dialysis tubing. After 24 hours one 500 ml medium change was performed, for a final effective dilution of 1/2500. The medium inside the dialysis membrane was removed, supplemented with 15% FBS and penicillin, streptomycin and Fungizone, and then was placed upon cystinotic fibroblasts. A control series was performed using the medium from outside the dialysis tubing, which has a MW cut-off of 3500 Daltons. This medium was supplemented exactly like the other medium. Three separate cystinotic cell lines, have been employed: GM00008 is homozygous for the 57 kb deletion; GM00018 does not have a specific defect listed on the Coriell site; GM00046 is homozygous for a 5 bp deletion at nucleotide 545 of exon 5 of the CTNS gene (545delTCCTT). Intracellular cystine is increased. This experiment has been done a total of five times. The cells were harvested by trypsinization at zero 24, 48, and 96 hours, and tested for cystine measurement. Over the four-day period there was a rapid and progressive decline in the cystine content to about 30% of control value for cells treated with the material inside the dialysis membrane, and little depletion from the cells treated with the media obtained from outside the dialysis membrane.

FIG. 11 shows a graph of relative cystine depletion levels by various portions (dialysate, dialysis fluid, sedementable fraction, supernatant) of media conditioned by CTNS-transfected or sialin-transfected cells.

FIG. 12 shows a graph of relative sialic acid depletion levels by various portions (dialysate, dialysis fluid, sedementable fraction, supernatant) of media conditioned by CTNS-transfected or sialin-transfected cells.

DEFINITIONS

Figure 1:
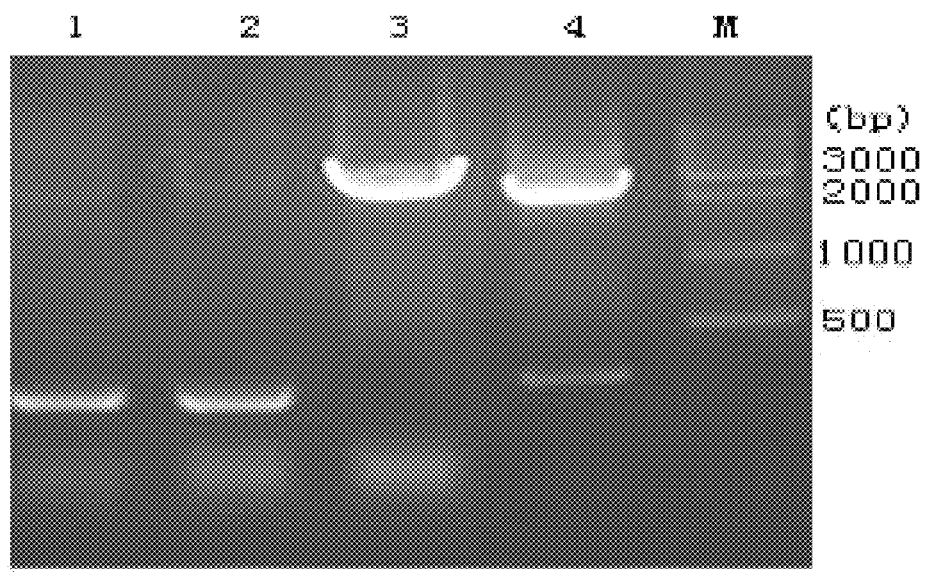
FIG. 1 shows an agarose gel of PCR identification of the Bacmid containing the cloned human cystinosin gene; Lane 1: negative control (Bacmid alone), Lane 2: unsuccessful cloning, Lane 3: human cystinosin gene in pFastBacHTA, and Lane 4. positive control (TGF-beta in pFastBac-GST).

As used herein the term "cystinosin replacement factor" or "CRF" refers to an agent or agents that perform the in vivo and/or in vitro function of cystinosin. A "CRF" may replace one or more (e.g. all) of the biological functions of endogenous wild-type cystinosin, including, but not limited to transport of lysosomal cystine, transporting cystine from the lysosomal interior to the cytosol, and/or depletion of cystine from lysosomes (e.g. cystinotic lysosomes). A "CRF" performs a biological function of cystinosin, typically by the same mechanism of action. A "CRF" comprises any compound (e.g. small molecule, polymer, etc.) and/or biomolecule (e.g. protein, peptide, nucleic acid, macromolecule, etc.) that replaces one or more biological functions of cystinosin. A "CRF" typically replaces the function of cystinosin in a subject suffering from cystinosis, with defective cystinosin function, and/or with an inadequate amount of cystinosin. A "CRF" may comprise proteins or polypeptides with similar sequence or structure to cystinosin, variants of cystinosin, truncated versions of cystinosin, mutated cystinosin, and/or combinations thereof. A "CRF" may comprise cystinosin (e.g. exogenously produced cystinosin).

As used herein the term "cystine depletion factor" or "CDF" refers to an agent or agents that depletes lysosomal cystine or causes a reduction in the concentration of cystine in lysosomes (e.g. cystinotic lysosomes). A CDF may be a cystinosin replacement factor or may deplete lysosomal cystine by a different mechanism, path, or biological function. In some embodiments, a "CDF" comprises any compound (e.g. small molecule, polymer, etc.) and/or biomolecule (e.g. protein, peptide, nucleic acid, macromolecule, etc.) that directly or indirectly (e.g. by acting on another factor (e.g. protein)) reduces the cystine concentration in lysosomes. In some embodiments, a "CDF" only reduces the cystine concentration in cystinotic lysosomes. A "CRF" may comprise proteins or polypeptides with similar sequence or structure to cystinosin, variants of cystinosin, truncated versions of cystinosin, mutated cystinosin, and/or combinations thereof. A "CRF" may comprise cystinosin (e.g. exogenously prodiced cystinosin).

The terms "protein" and "polypeptide" refer to compounds comprising amino acids joined via peptide bonds and may be used interchangeably.

As used herein, where "amino acid sequence" is recited herein to refer to an amino acid sequence of a protein or peptide molecule. An "amino acid sequence" can be deduced from the nucleic acid sequence encoding the protein. However, terms such as "polypeptide" or "protein" are not meant to limit the amino acid sequence to the deduced amino acid sequence, but include post-translational modifications of the deduced amino acid sequences, such as amino acid deletions, additions, and modifications such as glycolsylations and addition of lipid moieties.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide sequence comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

The term "polynucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The polynucleotide may be generated in any manner, including chemical synthesis, DNA replication, reverse transcription, or a combination thereof. The term "oligonucleotide" generally refers to a short length of single-stranded polynucleotide chain usually less than 30 nucleotides long, although it may also be used interchangeably with the term "polynucleotide."

The term "nucleic acid" refers to a polymer of nucleotides, or a polynucleotide, as described above. The term is used to designate a single molecule, or a collection of molecules. Nucleic acids may be single stranded or double stranded, and may include coding regions and regions of various control elements, as described below.

The term "a polynucleotide having a nucleotide sequence encoding a gene" or "a polynucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "vector" refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site; often along with other sequences. Eukaryotic cells are known to utilize promoters, enhancers, and termination and polyadenylation signals.

The term "type of nucleic acid" refers to a characteristic or property of a nucleic acid that can distinguish it from another nucleic acid, such as a difference in sequence or in physical form, such as occurs in different expression vectors, or as occurs with the presence of DNA and RNA, or as occurs with the presence of linear and super-coiled DNA, or as occurs with the presence of coding regions which encode different proteins, or as occurs with the presence of different control elements, or control elements which differ amongst themselves.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "host cell" refers to any cell capable of replicating and/or transcribing and/or translating a heterologous gene. Thus, a "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See, e.g., deWet et al., Mol. Cell. Biol. 7:725 (1987) and U.S. Pat. Nos. 6,074,859; 5,976, 796; 5,674,713; and 5,618,682; all of which are incorporated herein by reference), green fluorescent protein (e.g., GenBank Accession Number U43284; a number of GFP variants are commercially available from ClonTech Laboratories, Palo Alto, Calif.), chloramphenicol acetyltransferase, β-galactosidase, alkaline phosphatase, and horse radish peroxidase.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refers to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "sample" is used in its broadest sense. In one sense it can refer to biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. These examples are not to be construed as limiting the sample types applicable to the present invention.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, rectal, by injection (e.g., intravenously, subcutaneously, intratumorally, intraperitoneally, etc.) and the like.

As used herein, the term "pharmaceutical composition" refers to the combination of an active agent with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

DETAILED DESCRIPTION OF EMBODIMENTS

The present invention provides compositions and methods for providing factor replacement therapy. In some embodiments, the present invention provides methods for producing one or more factors useful in factor replacement therapy. In some embodiments, the present invention provides factors produced through recombinant protein expression, that find utility in factor replacement therapy. In some embodiments, a factor may be a protein (e.g. enzyme (e.g. cystinosin)), vitamin, nutrient, compound, composition, nucleic acid, small molecule, macromolecule, molecular complex, etc.

In some embodiments, the present invention provides methods for the production of factors for use in factor replacement therapy. In some embodiments, a subject is deficient in the endogenous production of one or more factors (e.g. cystinosin). In some embodiments, a subject produces defective factor, and is thereby deficient in normal/active/functioning factor. In some embodiments, a properly expressed factor is rendered defective through the action of another factor or factors, or by an unknown mechanism or pathway. In some embodiments, a factor deficiency (e.g. cystinosin deficiency) results in a disease, condition, and or disorder (e.g. cystinosis) in a factor deficient subject. In some embodiments, treatment of a disease or disorder (e.g. cystinosis) is performed by replacing the defective factor (e.g. protein (e.g. cystinosin)) with normal/active/functioning factor (e.g. produced exogenously (e.g. exogenously expressed cystinosin)), a variant of the factor, or another factor (e.g. related or unrelated). In some embodiments, replacement of, supplementing of, or compensation for the factor for which a subject is deficient provides therapy (e.g. curative, palliative) for the related condition (e.g. symptom reduction). In some embodiments, the factor provided in replacement therapy is the factor for which the subject is deficient (e.g. cystinosin). In some embodiments, the factor provided in replacement therapy is not the factor for which the subject is deficient. In some embodiments, the factor provided in replacement therapy is related to, a product of, and/or a by-product of expression of the factor for which the subject is deficient. In some embodiments, the factor provided in replacement therapy is a variant, mutant (e.g. >50% identity . . . >60% identity . . . >70% identity . . . >80% identity . . . >90% identity . . . >95% identity . . . >98% identity . . . >99% identity), or truncated version (e.g. >10% length of wild-type . . . >20% length of wild-type . . . >30% length of wild-type . . . >40% length of wild-type . . . >50% length of wild-type . . . >60% length of wild-type . . . >70% length of wild-type . . . >80% length of wild-type . . . >90% length of wild-type . . . >95% length of wild-type . . . >98% length of wild-type . . . >99% length of wild-type) of the factor for which the subject is deficient (e.g. cystinosin). In some embodiments, a factor or factors secreted by the cells expressing the factor for which the subject is deficient provides a replacement or supplement for the factor-deficient subject. In some embodiments, the factor for which the subject is deficient is secreted by the cells expressing the factor for which the subject is deficient, and the secreted factor provides a replacement or supplement for the factor-deficient subject. In some embodiments, one or more factors are purified and/or isolated from the liquid media. In some embodiments, one or more factors are purified and/or isolated along with a plurality of other compounds and compositions from the liquid media. In some embodiments, a mixture comprising the desired factor or factors and additional components from the liquid media provide a replacement and/or supplement for a factor deficiency.

In some embodiments, the present invention provides a composition configured to deplete lysosomes of cystine. In some embodiments, the present invention provides a composition configured to deplete cystinotic lysosomes of cystine. In some embodiments, the present invention provides a cystine depletion factor (CDF). In some embodiments, compositions and methods of the present invention provide a reduction in the level (e.g. concentration) of lysosomal cystine (e.g. in cystinotic lysosomes). In some embodiments, a CDF reduces the cystine level in cystinotic lysosomes. In some embodiments, a CDF reduces the cystine level in lysosomes through the same mechanism and/or pathway as cystinosin. In some embodiments, a CDF reduces the cystine level in lysosomes via an alternative mechanism and/or pathway to that utilized by cystinosin. In some embodiments, a CDF reduces the cystine level in cystinotic lysosomes by at least 50% (e.g. at least 50% . . . at least 60% . . . at least 70% . . . at least 80% . . . at least 90% . . . at least 950% . . . at least 98% . . . at least 99%). In some embodiments, CDF is cystinosin (e.g. exosome encapsulated cystinosin). In some embodiments, CDF is a factor (e.g. protein, polypeptide, nucleic acid, etc.) other than cystinosin. In some embodiments, CDF is produces and/or excreted from cells expressing cystinosin (e.g. exogenous cystinosin). In some embodiments, a CDF is a CRF.

In some embodiments, the present invention provides a composition configured to replace cystinosin in cystinosin-deficient subject, subject suffering from cystinosis, and/or subjects lacking functional cystinosin. In some embodiments, the present invention provides a composition configured to replace the function of a subject's endogenous cystinosin. In some embodiments, the present invention provides compositions comprising a cystinosin replacement factor (CRF). In some embodiments, a CRF is administered to a subject (e.g. subject suffering from cystinosis) to provide, replace, or supplement cystinosin function. In some embodiments, CRF performs the same biological functions as cystinosin. In some embodiments, CRF acts within the same biochemical pathways as cystinosin. In some embodiments, CRF is cystinosin (e.g. exosome encapsulated cystinosin). In some embodiments, CRF is a factor (e.g. protein, polypeptide, nucleic acid, etc.) other than cystinosin. In some embodiments, CRF is produces and/or excreted from cells expressing cystinosin (e.g. exogenous cystinosin). In some embodiments, a CRF is a CDF.

In some embodiments, the present invention provides exosomes (e.g. exosomes encapsulating CDF, CRF, and/or cystinosin), and methods of preparation, isolation, purification, administration, and use thereof. In some embodiments, exosomes comprises CDF, CRF, and/or cystinosin. In some embodiments, exosomes comprises lysosomal trans-membrane proteins. In some embodiments, exosomes are secreted from cells. In some embodiments, exosomes are secreted from cells (e.g. Sf9 cells) that have been engineered (e.g. transfected, transformed, etc.) to express cystinosin. In some embodiments, cells (e.g. Sf9 cells) that have been engineered (e.g. transfected, transformed, etc.) to express cystinosin secrete exosomes comprising CDF, CRF, and/or cystinosin. In some embodiments, cells that have been engineered to express cystinosin generate exosomes comprising cystinosin. In some embodiments exosomes (e.g. exosomes encapsulating CDF, CRF, and/or cystinosin) generated from cells are purified and/or isolated from other cellular and/or media components. In some embodiments, exosomes (e.g. exosomes encapsulating CDF, CRF, and/or cystinosin) are purified and/or isolated from some or all other cellular and/or media components by standard methodologies known to those in the art, not limited to: dialysis, centrifugation, chromatography, gel electrophoresis, filtration, etc. In some embodiments, the encapsulated contents (e.g. CDF, CRF, and/or cystinosin) of an exosome is co-purified with the exosome. In some embodiments, CDF, CRF, and/or cystinosin is purified and/or isolated from exosomes. In some embodiments, CDF, CRF, and/or cystinosin is not purified from exosomes before use and/or administration. In some embodiments, exosomes comprising (e.g. encapsulating) CDF, CRF, and/or cystinosin are administered to a subject to treat and/or prevent a disease, condition or disorder (e.g. cystinosis). In some embodiments, encapsulation of CDF, CRF, and/or cystinosin within exosomes does not inhibit the effectiveness of administration of cystinosin. In some embodiments, encapsulation of CDF, CRF, and/or cystinosin within exosomes enhances the effectiveness of administration of cystinosin. In some embodiments, encapsulation of CDF, CRF, and/or cystinosin within exosomes does not inhibit and/or enhances cellular uptake, subcellular localization, targeting to the lysosome, stability, etc. of CDF, CRF, and/or cystinosin. In some embodiments, exosomes (e.g. exosomes encapsulating CDF, CRF, and/or cystinosin) are about 50-100 nm (e.g. 60-80 nm) in diameter. In some embodiments, exosomes (e.g. exosomes encapsulating CDF, CRF, and/or cystinosin) are small enough to pass through a sterilization filter. In some embodiments, exosomes are freeze-thaw resistant. In some embodiments, exosomes provide a delivery system for CDF, CRF, and/or cystinosin by preferentially fusing with the endosomal system of cystinotic fibroblasts. In some embodiments, exosomes provide a transmembrane delivery system for CDF, CRF, and/or cystinosin.

In some embodiments, the present invention provides compositions and methods for expressing factors for use in factor replacement therapy. In some embodiments, factors for factor replacement therapy are expressed in a usable, stable, cell permeable, and/or effective form (e.g. encapsulated in exosomes). In some embodiments, encapsulation of factors within exosomes provides a delivery vehicle for the factor which allows cell entry and/or subcellular localization of the factor. In some embodiments, encapsulation within exosomes provides active factors. In some embodiments, encapsulation within exosomes provides soluble factors.

In some embodiments, the present invention provides cells which produce (e.g. express) a factor for which a subject is deficient. In some embodiments, the present invention provides cells which produce (e.g. express) a replacement factor (e.g. CRF) which performs one or more of the functions of the factor for which a subject is deficient. In some embodiments, cells are engineered (e.g. cloning, transformation, transfection, etc.) to produce a factor (e.g. protein) for use in the present invention. Techniques for engineering cells to produce a desired factor are understood in the art. In some embodiments, cells producing one or more factors are grown in liquid media. In some embodiments, cells secrete one or more factors into the liquid media within which they are grown. In some embodiments, cells secrete the factor (e.g. cystinosin), for which a subject is deficient, into the liquid media. In some embodiments, cells secrete one or more factors other than the one for which a subject is deficient (e.g. cystinosin) into the liquid media. In some embodiments, cells secrete a factor which is useful in treating a factor-deficient subject (e.g. a factor or factors other than the one for which the subject is deficient).

A variety of replacement factors may be generated using the methods described herein. In some embodiments, the replacement factor replaces cystinosin. In some embodiments, the replacement factor replaces a factor that is insoluble or substantially insoluble. In some embodiments, the replacement factor replaces a factor including, but not limited to, NiemannPick C disease (NPC), Sialic acid storage disease, Kufor-Rakeb syndrome, Batten Disease, etc.

In some embodiments, the present invention provides cloning a nucleic acid (e.g. gene) of interest into a vector. In some embodiments, the present invention provides transforming or transfecting a vector into a cell and/or cell line. In some embodiments, the present invention provides growing cells (e.g. in liquid media) under conditions such that a protein of interest is expressed (e.g. overexpressed). In some embodiments, the present invention provides collecting the media within which cells expressing a protein of interest have been grown. In some embodiments, the present invention provides isolating, concentrating, and/or purifying one or more factors, compounds, proteins, complexes, nutrients, etc. from the media within which cells expressing a protein of interest have been grown. In some embodiments, the present invention provides administering an isolated/purified fraction of the media within which cells expressing a protein of interest have been grown to a sample (e.g. cells) or subject deficient in the protein of interest. Isolated molecules or fractions may be added to other components, including, but not limited to, pharmaceutically acceptable buffers, other therapeutic agents, etc. In some embodiments, the present invention provides administering an isolated/purified fraction of the media within which cells expressing a protein of interest were grown. In some embodiments, an isolated/purified fraction of the media, within which cells expressing a protein of interest have been grown, compensates for the missing protein of interest in a sample or subject (e.g. provides therapy for the sample or subject). In some embodiments, a portion of the cells, cellular components, excreted factors, and/or the media in which they were grown is purified and/or isolated by any acceptable method including but not limited to dialysis, precipitation, chromatography, gel purification, centrifugation, ultracentrifugation, sedimentation, and/or combinations thereof.

In some embodiments, the present invention provides therapy for a subject suffering from cystinosis. In some embodiments, therapy provides one or more factors (e.g. cystine depletion factors) which address the accumulation of cystine in lysosomes caused by cystinosis. In some embodiments, the present invention provides replacement therapy for a subject suffering from cystinosis. In some embodiments, replacement therapy provides one or more replacement factors (e.g. cystinosin replacement factors) which perform one or more functions of the missing and/or deficient cystinosin. In some embodiments, the present invention provides compositions and methods to produce CDF or CRF for the treatment of cystinosis.

In some embodiments, a cystinosin gene (e.g. wild-type, mutated, truncated, etc.) is cloned into a suitable vector, and the vector is transformed or transfected into a cell or cell line. In some embodiments, cells containing the cystinosin gene are grown in liquid media under conditions such that cystinosin is expressed (e.g. overexpressed). In some embodiments, cystinosin is secreted from the cells. In some embodiments, cells producing cystinosin secrete other factors related to the expression of cystinosin. In some embodiments, cells producing cystinosin secrete one or more factors that find use as cystinosin replacement factors and/or cystine depletion factors. In some embodiments, cells, media, and or other factors (e.g. secreted factors (e.g. exosomes, secreted cystinosin, etc.), and purified and or isolated by suitable means. In some embodiments, the media from cystinosin-expressing cells is collected (e.g. by centrifugation, by filtration, etc.). In some embodiments, material secreted by cells (e.g. exosomes, cystinosin, etc.) are collected with the media. In some embodiments, the media is separated into fractions (e.g. by chromatography, by centrifugation, by ultracentrifugation, by filtration, by affinity, etc.). In some embodiments, one or more elements, vesicles (e.g. exosomes), compositions, compounds, proteins, etc. are isolated from the media. In some embodiments, the media is purified away from one or more contaminants. In some embodiments, the collected, fractionated, purified, and/or isolated media is configured to be administered as a factor replacement therapy for cystinosis. In some embodiments, the collected, fractionated, purified, and/or isolated media is configured to be administered as a lysosomal cystine depletion therapy for cystinosis. In some embodiments, administration of the collected, fractionated, purified, and/or isolated media provides a therapy for cystinosis. In some embodiments, the collected, fractionated, purified, and/or isolated media comprises soluble and active cystinosin. In some embodiments, the collected, fractionated, purified, and/or isolated media comprises cystinosin-related factors. In some embodiments, the collected, fractionated, purified, and/or isolated media comprises one or more CRF. In some embodiments, the collected, fractionated, purified, and/or isolated media comprises one or more CDF. In some embodiments, the collected, fractionated, sedimented, purified, and/or isolated media comprises factors capable of replacing, restoring, and/or compensating for endogenous cystinosin in subjects suffering from cystinosis. In some embodiments, the present invention provides administering isolated cystinosin as a therapy for cystinosis.

The compositions and methods of the present invention find use in the transfection of any number of cell types. Cells may be in vitro, in culture, ex vivo, or in vivo. In some embodiments, the systems and methods of the present invention find use in research, clinical, or diagnostic applications. In some embodiments, the present invention provides compositions and methods molecular biology techniques such as cloning, protein expression, protein purification, transforming and transfecting cells, growing cells in media, and other related methods described in the following references: Sambrook et al. (Ed.), "Molecular Cloning, a Laboratory Manual (3rd edition), Cold Spring Harbor Press and Cold Spring Harbor, N.Y. (2001), Ausubel et al. (Ed.), "Current Protocols in Molecular Biology," John Wiley & Sons Ltd., herein incorporated by reference in their entireties.

EXPERIMENTAL

Example 1

Cloning and Solubility

The human cystinosin encoding gene was subcloned into pFastBacHTA vector and the resulted construct was transformed into E. coli strain DH10Bac to generate recombinant Bacmid. The gene was cloned into the pFastBacHTA vector at EcoR1 and Not 1 restriction sites (restriction sites are underlined below).

```
   1 GAATTCATGA TCCGTAACTG GCTGACTATC TTCATCCTGT TCCCTCTGAA GCTGGTCGAG

61 AAGTGCGAGT CCTCCGTCAG CCTCACCGTG CCTCCCGTGG TGAAGCTGGA GAACGGTAGC

121 TCCACCAACG TCAGCCTCAC CCTGCGCCCC CCACTGAACG CCACCCTGGT GATCACCTTC

181 GAGATCACTT TCCGCTCCAA GAACATCACC ATCCTGGAGC TGCCTGACGA GGTGGTCGTG

241 CCTCCTGGTG TGACTAACTC TTCTTTCCAG GTGACCTCCC AGAACGTCGG ACAGCTGACC

301 GTGTACCTGC ACGGAAACCA CTCCAACCAG ACCGGACCCC GCATCCGCTT CCTCGTCATC

361 AGGTCCTCTG CTATCAGCAT CATCAACCAG GTGATCGGTT GGATCTACTT CGTGGCTTGG

421 AGCATCTCTT TCTACCCACA GGTCATCATG AACTGGAGGC GTAAGTCCGT GATCGGTCTG

481 TCCTTCGACT TCGTCGCTCT CAACCTGACC GGTTTCGTCG CTTACTCTGT GTTCAACATC

541 GGCCTCCTCT GGGTGCCCTA CATCAAGGAG CAGTTCCTCC TCAAGTACCC TAACGGTGTG

601 AACCCCGTCA ACTCCAACGA CGTGTTCTTC AGCCTGCACG CTGTCGTGCT GACCCTCATC

661 ATCATCGTCC AGTGCTGCCT GTACGAGCGT GGTGGCCAGC GCGTGTCCTG GCCTGCTATC

721 GGCTTCCTGG TCCTGGCCTG GCTGTTCGCT TTCGTCACTA TGATCGTGGC TGCTGTGGGT

781 GTGATCACCT GGCTGCAGTT CCTGTTCTGC TTCAGCTACA TCAAGCTGGC TGTCACCCTC

841 GTGAAGTACT TCCCTCAGGC TTACATGAAC TTCTACTACA AGAGCACTGA GGGTTGGTCC

901 ATCGGAAACG TGCTGCTGGA CTTCACCGGC GGCTCTTTCT CCCTGCTGCA GATGTTCCTG

961 CAGTCCTACA ACAACGACCA GTGGACCCTC ATCTTCGGAG ACCCCACTAA GTTCGGACTG

1021 GGTGTGTTCT CTATCGTCTT CGACGTGGTG TTCTTCATCC AGCACTTCTG CCTGTACCGC

1081 AAGCGCCCCG GATACGACCA GCTCAACTAA TAAGCGGCCG C
```

Figure 2:
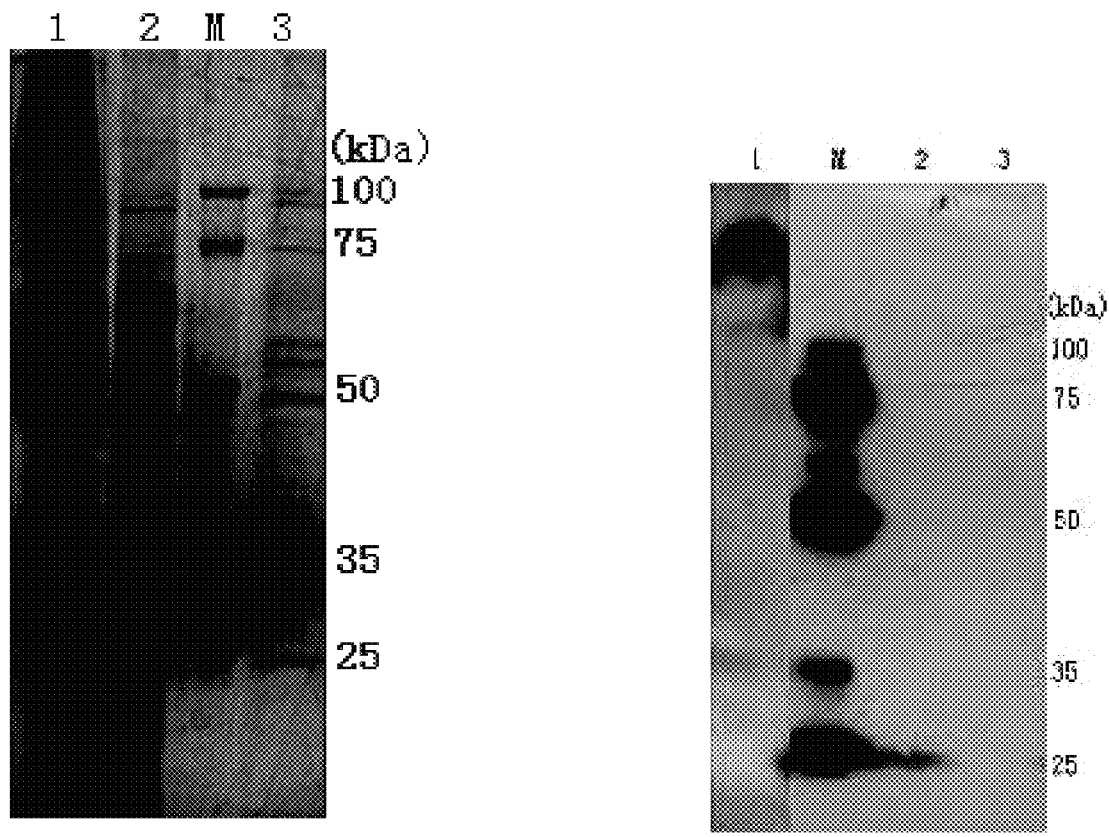
FIG. 2 shows Western blot analysis of P0 Cell pellet; Lane 1: whole cell lysate of P0 cell pellet, Lane 2: conditioned medium of P0, and Lane 3: whole cell lysate of Bacmid.

The positive colonies were selected by Gm, Tet and Kan, followed by PCR identification (SEE FIG. 1). The recombinant Bacmid was extracted and then transfected into Sf9 cells to generate the baculovirus, using CELLFECTIN (INVITROGEN), and incubated in HyQ liquid medium for 5 days at 27° C. after the cells were swollen. The supernatant was collected by centrifugation and designated as P0 virus. The cell pellet was used to detect the protein expression by SDS-PAGE and western blot analysis using monoclonal anti-His antibody. Target protein not visualized through western blot (SEE FIG. 2).

Multiplicity of infection (MOI) optimization was performed in sf9 cells. 10 ml 2×10$^6$/ml sf9 cells were infected at the MOI of 1, 2, 5, 10 and 20, and each 1 ml cell pellet was collected at 1 dpi, 2 dpi, 3 dpi and 4 dpi. The cells were analyzed by SDS-PAGE and western blot (SEE FIG. 3), and the result demonstrates that the protein level is highest 3 dpi.

Figure 6:
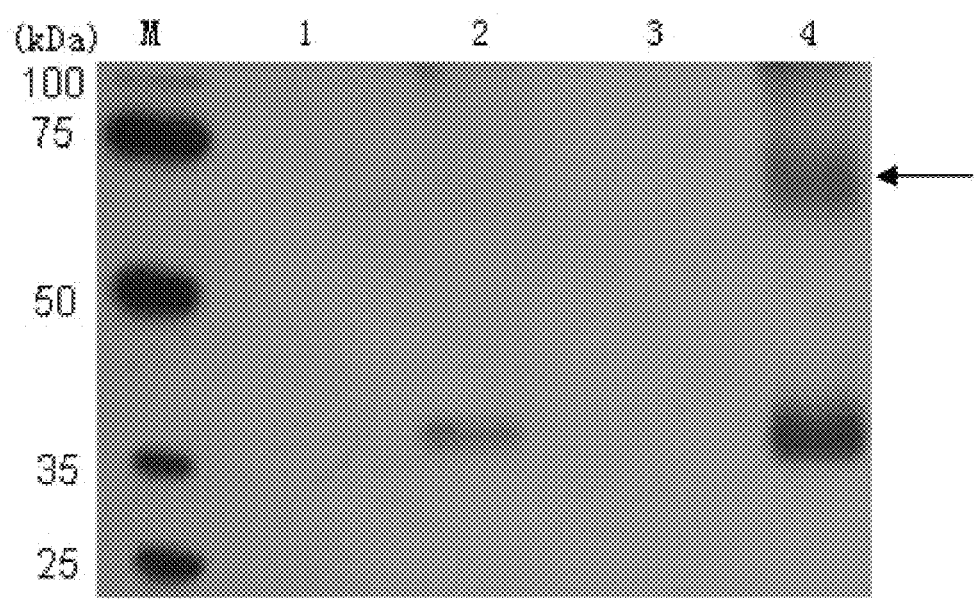
FIG. 6 shows Western blot of extraction test with urea: infected cells were suspended with 50 mM Tris.HCl, 300 mM NaCl, 2% Triton X-100, and pH 8.0 for 45 min on ice, and then treated with 8M urea, 50 mM Tris-HCl, 500 mM NaCl, pH 8.0 for about half an hour. Lane 1: whole cell lysate of Bacmid, Lane 2: whole cell lysate of 44783, Lane 3: supernatant treated with 8M urea, Lane 4: pellet treated with 8M urea. The Western blot shows the protein still exists in the pellet.

Solubility test of extracted cells demonstrates the protein is insoluble in all conditions tested (SEE FIGS. 4 and 5). The protein was insoluble even in the presence of 8M urea (SEE FIG. 6). The protein was also insoluble in SKL and thiourea (SEE FIG. 7). 6M Gu.HCl was used for the extraction and purification, no obvious target protein was obtained from the SDS-PAGE analysis, and the target protein precipitated during the dialysis in 20 mM imidazole elution from the western blot result (SEE FIG. 8).

Example 2

Replacement Therapy

Production of Cystinosin protein in a Baculoviral expression system is accomplished using GenScript, or another commercial source.

Figure 10:
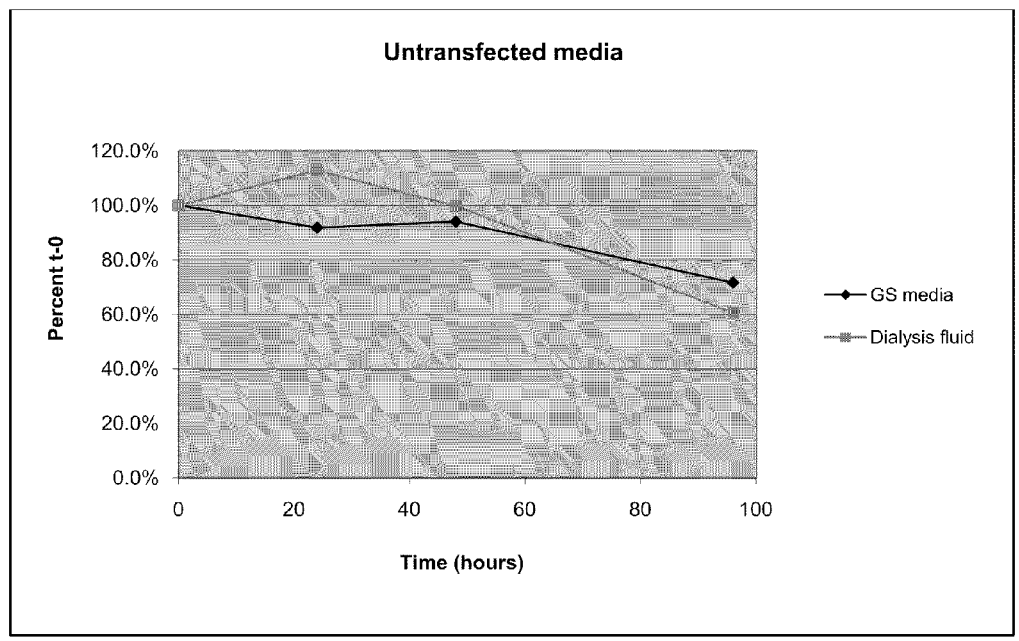
FIG. 10 shows cystine depletion of cystinotic fibroblasts by treatment with media from Sf9 cells not expressing human cystinosin; when conditioned medium from non-transfected Sf9 cells was dialyzed and prepared identically to that described and placed on cultured cystinotic fibroblasts, no difference in cystine depletion was seen between those cells treated with material from inside the dialysis membrane as compared top that from outside the membrane.

Purification of the soluble factor causing cystine depletion: the bioactive material which produces cystine depletion (SEE FIGS. 9 and 10 and Table 1) is separated by electrophoresis on 10-20% Tris-Tricine denaturing-SDS gels (Biorad; Cat #161-1162), blotted onto PVDF membranes (Biorad; Cat #162-0239), and the His epitope in the fusion-cystinosin protein is detected using an anti-His antibody, as performed by GeneScript (see attachment), as well as the anti-cystinosin mouse monoclonal antibody M09, clone 5G6 (Abnova/Novus Biologicals, Littleton, Colo.; Cat #H00001497-M09); primary antibody hybridization signals are detected using a rabbit anti-mouse HRP-conjugated secondary antibody (Chemicon International, Temecula, Calif.; Cat #AP124P) and chemiluminiscent detection (ChemiLucent™ western blot detection system; Chemicon International; Cat #2606). 6×His tagged-cystinosin is purified by Ni-NTA affinity column purification (Qiagen Inc; Cat #31014).

etry of cystinosin versus standard protein band intensities, using a BioRad ChemiDoc XRS system, available in the Department of Pediatrics Research core.

The putative soluble isoform which is non-dialyzable, and which causes the observed cellular cystine depletion, may be the product of an alternative splice site, recognized by the Sf9 cells. This isoform is identified by use of both anti-his and anti-cystinosin antibodies, as well as by Northern blot of message derived from the transfected Sf9 cells. Northern blotting is carried out using cell pellets from the tranfected Sf9 cells using the NorthernMax kit from Ambion (catalog number: A1940). RNA probes are made via RT-PCR using commercially available primers to CTNS (Qiagen, catalog numbers: QT00999257, QT00999264; QIAGEN OneStep RT-PCR Kit, catalog number: 210210).

TABLE 1

Cystine Depletion by CTNS-transfected Sf9 Media

| | nmols cystine per mg protein by trial | | | | | | | |
|---|---|---|---|---|---|---|---|---|
| Time (hours) | GM00008 | GM00008 | GM00046 | GM00018 | GM00008 | Average | StDev | t-test |
| 0 | 4.56 | 3.48 | 2.99 | 3.26 | 3.80 | 3.62 | 0.54 | NA |
| 24 | 3.68 | 1.71 | 2.36 | 2.67 | 4.14 | 2.91 | 0.88 | 0.660 |
| 48 | 1.42 | 1.21 | 2.65 | 1.88 | 2.22 | 1.88 | 0.52 | 0.004 |
| 96 | 0.53 | 1.01 | 2.10 | 0.93 | 1.00 | 1.11 | 0.52 | 0.021 |
| 24 (control) | NA | 2.77 | 2.59 | 3.23 | 4.08 | 3.17 | 0.58 | |
| 48 (control) | NA | 3.09 | 3.43 | 3.15 | 3.53 | 3.30 | 0.18 | |
| 96 (control) | NA | 2.29 | 2.70 | 2.48 | 4.36 | 2.96 | 0.82 | |

| | as fraction of t – 0 | | | | | | | |
|---|---|---|---|---|---|---|---|---|
| Time (hours) | GM00008 | GM00008 | GM00046 | GM00018 | GM00008 | Average | StDev | t-test |
| 0 | 1.00 | 1.00 | 1.00 | 1.00 | 1.00 | 1.00 | 0.00 | NA |
| 24 | 0.81 | 0.49 | 0.79 | 0.82 | 1.09 | 0.80 | 0.21 | 0.286 |
| 48 | 0.31 | 0.35 | 0.89 | 0.58 | 0.58 | 0.54 | 0.23 | 0.009 |
| 96 | 0.12 | 0.29 | 0.70 | 0.29 | 0.26 | 0.33 | 0.22 | 0.008 |
| 24 (control) | NA | 0.80 | 0.87 | 0.99 | 1.07 | 0.93 | 0.12 | |
| 48 (control) | NA | 0.89 | 1.15 | 0.97 | 0.93 | 0.98 | 0.11 | |
| 96 (control) | NA | 0.66 | 0.90 | 0.76 | 1.15 | 0.87 | 0.21 | |

Purified protein is quantified using the BCA Protein Assay Kit (Pierce Biotechnology, Cat #23225. If necessary, the N-terminal 6×His tag and V5 epitopes is removed from the fusion protein by TEV protease digestion before use in further experiments. Purified cystinosin protein is analyzed and its sequence verified by peptide sequencing in the peptide core at the University of Michigan.

A C-terminal fusion-cystinosin expression construct, by cloning the CTNS ORF into the BaculoDirect™ Baculovirus C-term expression vector (Invitrogen; Cat #12562-013), or expression cystinosin in another system, such as the yeast *Pichia pastoris*, or mammalian cells is also contemplated.

Quantitation of purified His-tagged cystinosin is performed by comparative densitometry. Aliquots of purified cystinosin is run on 4-20% Tris-Tricine denaturing-SDS gels (Biorad; Cat #161-1162), along with the Smart His-tagged Protein Standard (GenScript Cat #MM0904-100), which contains several highly purified His-tagged proteins at known concentrations. After electrophoresis, the protein is blotted onto PVDF membranes (Biorad; Cat #162-0239), and the hexahistidine tags in the separated proteins are visualized using the His-Detector™ Western Blot Kit, HRP Chemiluminescent kit (KPL Inc, Cat #24-00-02). This kit provides sensitive, reproducible labeling of 6-His-tagged proteins that is less subject to variations in signal intensity than anti-His tag antibodies, and hence can provide better quantitation. Cystinosin concentration is estimated by comparative densitom- Measurement of the effect of Baculovirus-produced cystinosin on the cystine content of cystinotic fibroblasts is performed using multiple separate lines of cultured diploid epithelial fibroblasts (cystinotic and normal). The exocytosis rate in such cells was determined by following the loss of a membrane-impermeant marker using $^3$H-mannitol. It was estimated that over a 24 hour period in tissue culture fibroblasts will pinocytose approximately 13 μl/$10^6$ cells, and lose via exocytosis, approximately 60% of the initial lysosomal contents. Using data from a successful clinical trial treating patients with another lysosomal storage diseases, MPS II, at a starting dose of idursulfase of 0.15 mg/kg every other week, and assuming that the infused protein is initially equilibrated in the vascular space for uptake by the liver and other tissues, it was calculated that the concentration initially achieved in the circulation would be would be 1.88 mg/l of idursulfase (assuming a vascular volume of 8%). This results in initial delivery of 1.88 ng/μl×13 μl/106 cells/24 hrs=~24 ng of cystinosin/million cells/24 hrs. If cystinosin behaves like a membrane impermeant marker, about 60% would be lost in this interval, hence a minimum estimate of cystinosin retention will be 24×0.4=~10 ng/$10^6$ cells/24 hrs.

Example 3

CDF Characterization

Experiments were conducted during development of embodiments of the present invention to determine the capacity of CTNS-transfected *Spodoptera* conditioned medium, sialin transfected media, or putative exosomes prepared from each medium, to deplete either cystine in cystinotic cells, or sialic acid in ISSD cells after 96 h exposure.

Media was conditioned with either CTNS-transfected *Spodoptera* or sialin. The cells and media were either (1) dialyzed against a 3500 molecular weight cutoff membrane, and the dialysis fluid and dialysate were both collected; or (2) the media was separated into sedimentable and supernatant fractions by ultracentrifugation at 140,000×g of each medium followed by resuspension of the sedimentable fraction in Ham's F12 tissue culture medium. ISSD cells were exposed to the dialysis fluid, dialaysate, sedimentable fraction, or supernatent for 96 hours, and the cystein concentration was measured to determine the capacity of each to deplete cystine from the cells. Cystine content was normalized to the mean of the two control plates (3.2 nmol/mg protein) and set at 100%.

At 96 h, the CTNS-transfected dialysate caused a decline in the cell cystine content to about 33% of control, a value essentially equaled by the sedimentable fraction of that medium (SEE FIG. 11). None of the other conditions caused greater than 50% depletion at 96 h. These data demonstrate that the CDF resides in the dialysate of CTNS-transfected *Spodoptera* cells and can be sedimented by 140,000×g. The supernatant, above the sedimentable fraction, does not cause cystine depletion, consistent with CDF being contained in exosomes. No significant cystine depletion occurred in cells incubated with sialin-transfected medium or its sedimentable fraction. However, the dialysate and sedimentable fraction of the sialin-transfected medium we both able to deplete sialic acid in cells, while the other conditions were unable to do so (SEE FIG. 12).

Example 4

Western Blot Analysis

Figure 13:
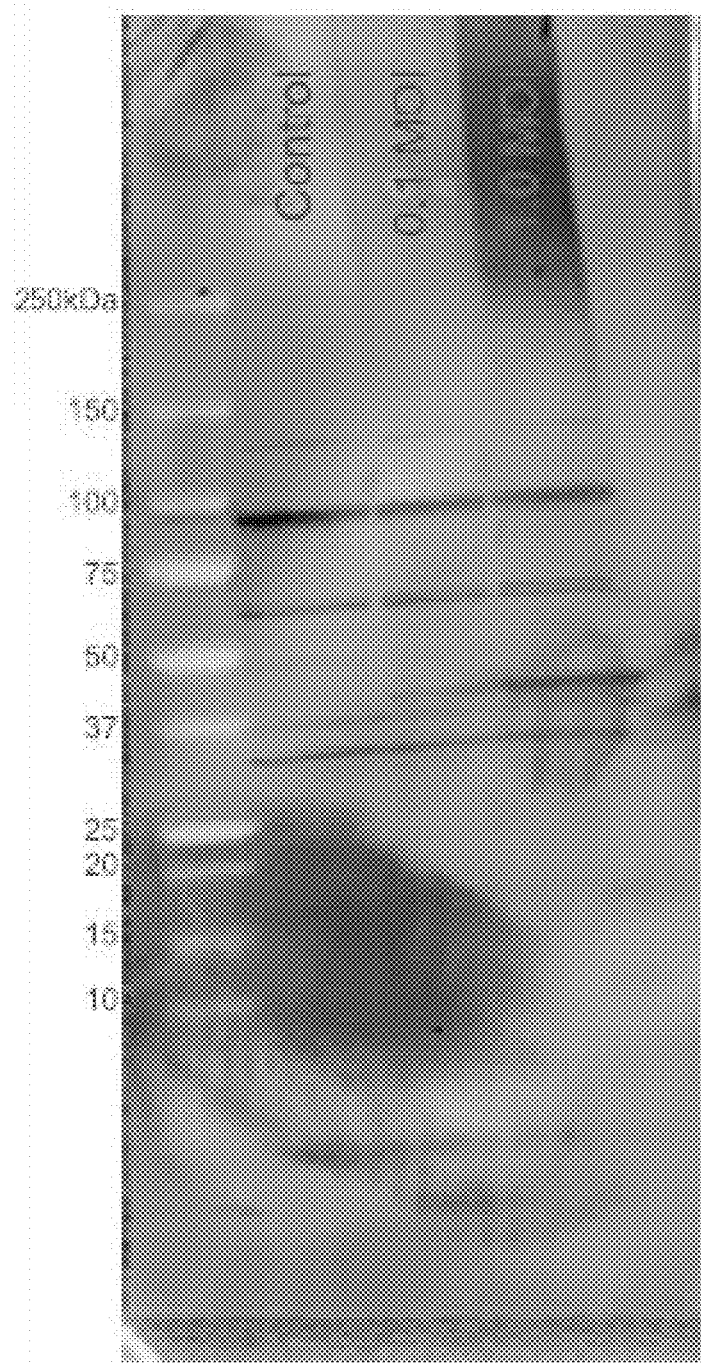
FIG. 13 shows Western blot analysis of protein expression from cystinosin-transfected Sf9 cells. Data are consistent with expression of human cystinosin in the Baculovirus infected Sf9 cells.

Experiments were conducted during development of embodiments of the present invention to confirm the expression of human cystinosin in cells transfected with the gene for cystinosin (CTNS). A Western blot was made of cell lysate from Sf9 cells infected with the CTNS-containing baculovirus made by Genscript (SEE FIG. 13).

Sf9 cells were grown in 60 mm plates and infected at multiplicity of infection (MOI) of zero, 0.1, and 1.0 and then harvested 4 days post infection by scraping and resuspended in 4×SDS Laemmli buffer. After brief sonication, the samples were boiled at 100° C. for 5 minutes. SDS-PAGE was performed using 10 μL from these samples in each lane. The gel was run was at 120V constant voltage at 64 mA-21 mA, for 107 minutes. Gel transfer was done at 100V constant, 0.64 A-0.85 A mA for one hour. SC 100703 mouse mAb against human cystinosin was used at a concentration of 1:100 with secondary Promega HRP goat anti-mouse IgG, at a concentration of 1:2000. Blocking and Ab incubation buffer were 5% NFDM in PBST and ECL-plus from GE Healthcare. The blot was imaged on a Typhoon Trio scanner. A band, slightly larger than 37 kDa (arrow), is visible only in the Baculovirus infected samples (i.e. cystinosin-transfected samples). The MW of this band is the approximate MW of cystinosin with 367 aminoacids. This band is absent in the non-CTNS transfected Sf9 cells (control), and shows an increase in density with MOI (1.0 MOI>0.1 MOI), indicating expression of the transgene. The data demonstrate expression of a polypeptide consistent with expression of human cystinosin in the Baculovirus infected Sf9 cells.

All publications and patents mentioned in the present application and/or listed below are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

REFERENCES

The following references are herein incorporated by reference in their entirety:

Gahl W A, Thoene J G, Schneider J A: Cystinosis. New Eng J Med. 2002; 347:111-121.

Gene Therapy Patient Dies, Trial Shutdown. Associated Press, Jul. 26, 2007.

R. J. Anderson, D. Cairns, W. A. Cardwell, M. Case, P. W. Groundwater, A. G. Hall, L. Hogarth, A. L. Jones, O. Meth-Cohn, P. Suryadevara, A. Tindall & J. G. Thoene: Design, Synthesis and Initial In Vitro Evaluation of Novel Prodrugs for the Treatment of Cystinosis. Letters in Drug Design & Discovery 3, 336-345, 2006

Thoene J A Review of the Role of Enhanced Apoptosis in the Pathophysiology of Cystinosis Mol Genet Metab. 2007: 92, 292-298.

Palacin M, Goodyear G, Nunes V, Gasparini P. Cystinuria in C. Scriver, A. Beaudet, W. Sly, D. Valle, eds. *The Metabolic and Molecular Bases of Inherited Disease*, 8th edition, McGraw Hill, 4909-4932, 2001.

Town M, Cherqui S, Attard M, Forestier L, Whitmore S A, Callen D F, Gribouval O, Broyer M, Bates G P, van't Hoff W, Antignac C. A novel gene encoding an integral membrane protein is mutated in nephropathic cystinosis. Nature Genet 18: 319-324, 1998.

Thoene, J., Oshima, R., Crawhall, J., Olson, D., & Schneider, J: Cystinosis: Intracellular Cystine Depletion by Aminothiols in Vitro and in Vivo. J. Clin. Invest. 1976; 58:180-189.

Shotelersuk, V., Larson, D., Anikster, Y., McDowell, G., Lemons, R., Bernardini, I., Guo, J., Thoene, J., Gahl, W. CTNS mutations in an American-based population of cystinosis patients. Am Journal of Human Genetics, 1998; 63:1352-1362.

Muenzer J, Gucsavas-Calikoglu M, McCandless S, Schuetz T, Kimura A. A phase I/II clinical trial of enzyme replacement therapy in mucopolysacchardidosis II (Hunter syndrome) Mol Gen and Metab 2007, 90: 329-337.

Lemons, R., Forster, S, and Thoene, J. Protein microinjection by protease permeabilization of fibroblasts. Anal. Biochem. 1988; 172: 219-227.

Pisoni, R. L., Acker, T. L., Lemons, R. M., Lisowski, K. M., and Thoene, J. G. A cystine-specific lysosomal transport system provides a major route for the delivery of thiol to human fibroblast lysosomes: Role in supporting lysosomal proteolysis, J. Cell Biol., 1990; 110:327-335.

Lowry O, Roseborough N, Farr A, Randall R Protein measurement with the Folin phenol reagent 1951 J Biol Chem 193; 265-275.

Shotelersuk, V., Larson, D., Anikster, Y., McDowell, G., Lemons, R., Bernardini, I., Guo, J., Thoene, J., Gahl, W. CTNS mutations in an American-based population of cystinosis patients. Am Journal of Human Genetics, 1998; 63:1352-1362.

We claim:

1. A composition comprising extracellular vesicles produced by transfected cells in culture, said extracellular vesicles comprising recombinant human cystinosin.

2. The composition of claim 1, wherein said composition depletes cystine from cystinotic lysosomes.

3. The composition of claim 1, wherein said composition is obtained from a liquid media in contact with said transfected cells.

4. The composition of claim 1, wherein said recombinant cystinosin is within the extracellular vesicles.

5. The composition of claim 1, wherein said recombinant cystinosin functions as a replacement for endogenous cystinosin in a subject suffering from cystinosis.

6. The composition of claim 1, further comprising a pharmaceutically acceptable buffer.

7. A method for treating cystinosis, comprising: administering a composition of claim 1 to a subject suffering from cystinosis.

8. A method of treating cystinosis, comprising: administering a composition of claim 5 to a subject suffering from cystinosis.

9. The method of claim 7, wherein said transfected cells comprise Sf9 cells.

10. The method of claim 8, wherein said transfected cells comprise Sf9 cells.

* * * * *

SEQUENCE LISTING

<160> NUMBER OF SEQ ID NOS: 1

<210> SEQ ID NO 1
<211> LENGTH: 1121
<212> TYPE: DNA
<213> ORGANISM: Artificial Sequence
<220> FEATURE:
<223> OTHER INFORMATION: Synthetic

<400> SEQUENCE: 1

| | | | | | |
|---|---|---|---|---|---|
| gaattcatga | tccgtaactg | gctgactatc | ttcatcctgt | tccctctgaa | gctggtcgag | 60 |
| aagtgcgagt | cctccgtcag | cctcaccgtg | cctcccgtgg | tgaagctgga | gaacggtagc | 120 |
| tccaccaacg | tcagcctcac | cctgcgcccc | ccactgaacg | ccaccctggt | gatcaccttc | 180 |
| gagatcactt | tccgctccaa | gaacatcacc | atcctggagc | tgcctgacga | ggtggtcgtg | 240 |
| cctcctggtg | tgactaactc | ttctttccag | gtgacctccc | agaacgtcgg | acagctgacc | 300 |
| gtgtacctgc | acggaaacca | ctccaaccag | accggacccc | gcatccgctt | cctcgtcatc | 360 |
| aggtcctctg | ctatcagcat | catcaaccag | gtgatcggtt | ggatctactt | cgtggcttgg | 420 |
| agcatctctt | tctacccaca | ggtcatcatg | aactggaggc | gtaagtccgt | gatcggtctg | 480 |
| tccttcgact | tcgtcgctct | caacctgacc | ggtttcgtcg | cttactctgt | gttcaacatc | 540 |
| ggcctcctct | gggtgcccta | catcaaggag | cagttcctcc | tcaagtaccc | taacggtgtg | 600 |
| aaccccgtca | actccaacga | cgtgttcttc | agcctgcacg | ctgtcgtgct | gaccctcatc | 660 |
| atcatcgtcc | agtgctgcct | gtacgagcgt | ggtggccagc | gcgtgtcctg | gcctgctatc | 720 |
| ggcttcctgg | tcctggcctg | gctgttcgct | ttcgtcacta | tgatcgtggc | tgctgtgggt | 780 |
| gtgatcacct | ggctgcagtt | cctgttctgc | ttcagctaca | tcaagctggc | tgtcaccctc | 840 |
| gtgaagtact | tccctcaggc | ttacatgaac | ttctactaca | agagcactga | gggttggtcc | 900 |
| atcggaaacg | tgctgctgga | cttcaccggc | ggctctttct | ccctgctgca | gatgttcctg | 960 |
| cagtcctaca | caacgacca | gtggaccctc | atcttcggag | accccactaa | gttcggactg | 1020 |
| ggtgtgttct | ctatcgtctt | cgacgtggtg | ttcttcatcc | agcacttctg | cctgtaccgc | 1080 |
| aagcgccccg | gatacgacca | gctcaactaa | taagcggccg | c | | 1121 |